United States Patent
Mansky et al.

(10) Patent No.: US 11,771,329 B2
(45) Date of Patent: Oct. 3, 2023

(54) FLEXIBLE TEMPERATURE SENSING DEVICES FOR BODY TEMPERATURE SENSING

(71) Applicant: Apple Inc., Cupertino, CA (US)

(72) Inventors: Paul Mansky, San Francisco, CA (US); Xiaofan Niu, San Jose, CA (US); James C. Clements, Campbell, CA (US); Mahmut Tosun, Cupertino, CA (US); Michael Vosgueritchian, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 340 days.

(21) Appl. No.: 17/031,559

(22) Filed: Sep. 24, 2020

(65) Prior Publication Data

US 2022/0087534 A1     Mar. 24, 2022

(51) Int. Cl.
  *A61B 5/01*   (2006.01)
  *A61B 5/00*   (2006.01)
  *G01K 13/20*  (2021.01)

(52) U.S. Cl.
  CPC .............. *A61B 5/01* (2013.01); *A61B 5/6892* (2013.01); *G01K 13/20* (2021.01); *A61B 2562/0271* (2013.01); *A61B 2562/043* (2013.01)

(58) Field of Classification Search
  CPC ...................................... G01K 13/20
  (Continued)

(56) References Cited

U.S. PATENT DOCUMENTS 4,935,345 A   6/1990   Guilbeau
5,623,594 A   4/1997   Swamy
(Continued)

FOREIGN PATENT DOCUMENTS

CA   2654084     12/2007
CN   103873636    6/2014
(Continued)

OTHER PUBLICATIONS

Maurer et al., "eWatch: a wearable sensor and notification platform," International Workshop on Wearable and Implantable Body Sensor Networks (BSN'06), Apr. 3-5, 2006, 4 pages.

*Primary Examiner* — Mirellys Jagan
(74) *Attorney, Agent, or Firm* — Brownstein Hyatt Farber Schreck, LLP

(57) ABSTRACT

Embodiments include a temperature sensing device that includes a temperature sensor stack that includes a flexible substrate and an array of temperature sensors coupled to the flexible substrate. Each temperature sensor in the array of temperature sensors can include a conductive material defining a continuous pattern extending from a first node to a second node, a first set of conductive traces coupled to the flexible substrate, and a second set of conductive traces coupled to the flexible substrate. The temperature sensing device can include a processing circuit configured to apply an electrical signal across the conductive material of each temperature sensor using the first set of conductive traces, detect an effect of the conductive material of each temperature sensor on the electrical signal using the second set of conductive traces, and determine a temperature for the temperature sensors in the array using the detected effects of the conductive material on the electrical signal.

13 Claims, 15 Drawing Sheets

(58) Field of Classification Search
USPC .................................. 374/100, 208, 166
See application file for complete search history.

(56) References Cited

U.S. PATENT DOCUMENTS

| | | |
|---|---|---|
| 6,639,395 B2 | 10/2003 | Male |
| 6,741,470 B2 | 5/2004 | Isenburg |
| 7,299,090 B2 | 11/2007 | Koch |
| 7,416,332 B2 | 8/2008 | Rountree et al. |
| 7,479,116 B2 | 1/2009 | Yarden et al. |
| 7,622,896 B2 | 11/2009 | Nakagawa |
| 7,852,710 B2 | 12/2010 | Kelly et al. |
| 8,292,495 B2 | 10/2012 | Bieberich et al. |
| 8,292,502 B2 | 10/2012 | Bieberich et al. |
| 8,304,851 B2 | 11/2012 | Trifonov |
| 8,550,702 B2 | 10/2013 | Campbell et al. |
| 8,617,381 B2 | 12/2013 | Sun et al. |
| 8,649,998 B2 | 2/2014 | Yarden et al. |
| 8,954,288 B2 | 2/2015 | Aljabari |
| 9,300,157 B2 | 3/2016 | Bergqvist et al. |
| 9,304,520 B2 | 4/2016 | Cheng |
| 9,326,097 B2 | 4/2016 | Sen et al. |
| 9,438,071 B1 | 9/2016 | Heiberg |
| 9,562,869 B2 | 2/2017 | Mueller et al. |
| 9,599,520 B2 | 3/2017 | Angeli et al. |
| 9,671,296 B2 | 6/2017 | Niederberger et al. |
| 9,976,914 B2 | 5/2018 | Radhakrishnan et al. |
| 9,990,172 B2 | 6/2018 | Komaromi et al. |
| 9,993,178 B2 | 6/2018 | Panescu et al. |
| 10,151,527 B2 | 12/2018 | Rusnack et al. |
| 10,197,457 B2 | 2/2019 | Jang et al. |
| 10,238,301 B2 | 3/2019 | Weebadde et al. |
| 10,244,985 B1 | 4/2019 | Sayani et al. |
| 10,309,840 B2 | 6/2019 | Kalyanasundaram |
| 10,371,584 B2 | 8/2019 | Kim et al. |
| 10,500,087 B2 | 12/2019 | Thomas et al. |
| 10,750,951 B1 | 8/2020 | Prachar |
| 10,827,931 B2 | 11/2020 | Meyerson et al. |
| 10,987,054 B2 | 4/2021 | Pandya et al. |
| 11,224,344 B2 | 1/2022 | Ellis et al. |
| 11,253,157 B2 | 2/2022 | Tanaka et al. |
| 11,406,268 B2 | 8/2022 | Tsuchimoto |
| 11,419,549 B2 | 8/2022 | Shimuta |
| 2005/0139250 A1 | 6/2005 | DeSteese et al. |
| 2008/0043811 A1* | 2/2008 | Thomsen, III ......... G01K 7/186 374/E7.023 |
| 2008/0234004 A1 | 9/2008 | Logue et al. |
| 2010/0245090 A1* | 9/2010 | Smith ...................... G01K 7/04 340/573.1 |
| 2011/0119018 A1 | 5/2011 | Skarp |
| 2011/0245713 A1 | 10/2011 | Rensen et al. |
| 2012/0128024 A1 | 5/2012 | Tsuchida et al. |
| 2014/0163765 A1 | 6/2014 | Jain et al. |
| 2014/0334517 A1* | 11/2014 | Blundell ................ G01K 1/143 374/44 |
| 2017/0007167 A1 | 1/2017 | Kostic et al. |
| 2017/0288452 A1 | 10/2017 | Adams et al. |
| 2018/0004169 A1 | 1/2018 | Matsuzaki et al. |
| 2018/0028072 A1 | 2/2018 | Shi |
| 2018/0206729 A1 | 7/2018 | Wang et al. |
| 2019/0175024 A1 | 6/2019 | Lan et al. |
| 2021/0121071 A1 | 4/2021 | Mensch et al. |
| 2021/0186336 A1 | 6/2021 | Bellifemine et al. |
| 2021/0264346 A1 | 8/2021 | Momayez et al. |
| 2021/0278290 A1 | 9/2021 | Ghoreyshi et al. |
| 2021/0404883 A1 | 12/2021 | Rahmani et al. |
| 2022/0000370 A1 | 1/2022 | Blom et al. |
| 2022/0373404 A1 | 11/2022 | Clements et al. |

FOREIGN PATENT DOCUMENTS

| | | | |
|---|---|---|---|
| CN | 112444322 | 3/2021 | |
| DE | 102009003848 A1 * | 11/2010 | ............... G01K 1/02 |
| JP | 2012132818 | 7/2012 | |
| KR | 20180097191 | 8/2018 | |
| WO | WO 13/185679 | 12/2013 | |
| WO | WO 18/152566 | 8/2018 | |
| WO | WO 20/249665 | 12/2020 | |

* cited by examiner

FLEXIBLE TEMPERATURE SENSING DEVICES FOR BODY TEMPERATURE SENSING

FIELD

The described embodiments relate generally to devices, methods, and systems for measuring a physiological parameter of a user. More particularly, the present embodiments relate to flexible temperature sensing devices for sensing body temperature.

BACKGROUND

Physiological sensors, such as temperature measurement devices, heart monitoring devices, or blood oxygen level sensors, are increasingly being incorporated into different types of wearable devices such as smart watches, clothing, glasses, and/or other objects, such as beds, furniture, and so on. The incorporation of physiological sensors into these types of objects can facilitate health monitoring of a user during their routine normal everyday actions. For example, a person typically only measures their temperature when they suspect they are sick or for some other purpose such as natural family planning. In these cases, a person measuring her or his temperature is not part of their daily routine, and these temperature measurements are typically infrequent. In order to track a person's temperature more consistently, temperature measurement devices may be incorporated into various objects such as smart watches, clothing, bedding, and so on. In some cases, it may be desirable to have sensing devices that are thinner, more flexible, and/or more durable such that they may have minimal impact on the user and/or function more reliably when incorporated into such devices.

SUMMARY

A first set of embodiments is directed to temperature sensing device that includes a temperature sensor stack including a flexible substrate, and an array of temperature sensors coupled to the flexible substrate. Each temperature sensor in the array of temperature sensors can include a conductive material forming a continuous pattern on the flexible substrate that extends from a first node to a second node, a first conductive trace positioned on the flexible substrate and coupled to the first node, and a second conductive trace positioned on the flexible substrate and coupled to a second node. The temperature sensing device can also include a processing circuit configured to apply an electrical signal across the conductive material of each temperature sensor using the first and second conductive traces, detect an effect of the conductive material of each temperature sensor on the electrical signal using the first and second conductive traces, and determine a temperature for temperature sensors in the array of temperature sensors using the detected effect of the conductive material on the electrical signal.

Another set of embodiments is directed to a temperature sensing device that includes a substrate comprising a first side and a second side. A temperature sensor including a conductive material can be coupled to the first side of the substrate and define a continuous pattern extending from a first node to a second node. The temperature sensing device can include a first set of conductive traces on the substrate and comprising a first trace coupled to the first node and a second trace coupled to the second node. The first set of conductive traces can be operative to apply an electrical signal across the temperature sensor. The temperature sensing device can include a second set of conductive traces on the substrate and comprising a third trace coupled to the first node and a fourth trace coupled to the second node. The second set of conductive traces can be operative to detect an effect of the conductive material on the electrical signal. The temperature sensing device can include a cover layer coupled to the first side of the substrate and positioned over the conductive material, the first set of conductive traces, and the second set of conductive traces. The cover layer can define an opening, and the first and second sets of conductive traces extend from the temperature sensor to the opening.

Another set of embodiment is directed to temperature sensing device that includes a flexible substrate including a first side and a second side. A temperature sensor comprising a conductive material can be coupled to the first side of the flexible substrate and define a continuous pattern extending from a first node to a second node. The temperature sensing device can include a first set of conductive traces formed on the first side of the flexible substrate, where the first set of conductive traces include a first trace coupled to the first node and a second trace coupled to the second node. The temperature sensing device can also include a second set of conductive traces formed on the second side of the flexible substrate, where the second set of conductive traces include a third trace and a fourth trace. A first electrical interconnect can couple the first trace to the third trace, and a second electrical interconnect can couple the second trace to the fourth trace. A first cover layer can be coupled to the first side of the flexible substrate and cover the temperature sensor and the first set of conductive traces. A second cover layer can be coupled to the second side of the flexible substrate and cover the second set of conductive traces.

BRIEF DESCRIPTION OF THE DRAWINGS

The disclosure will be readily understood by the following detailed description in conjunction with the accompanying drawings, wherein like reference numerals designate like structural elements, and in which.

Figure 1:
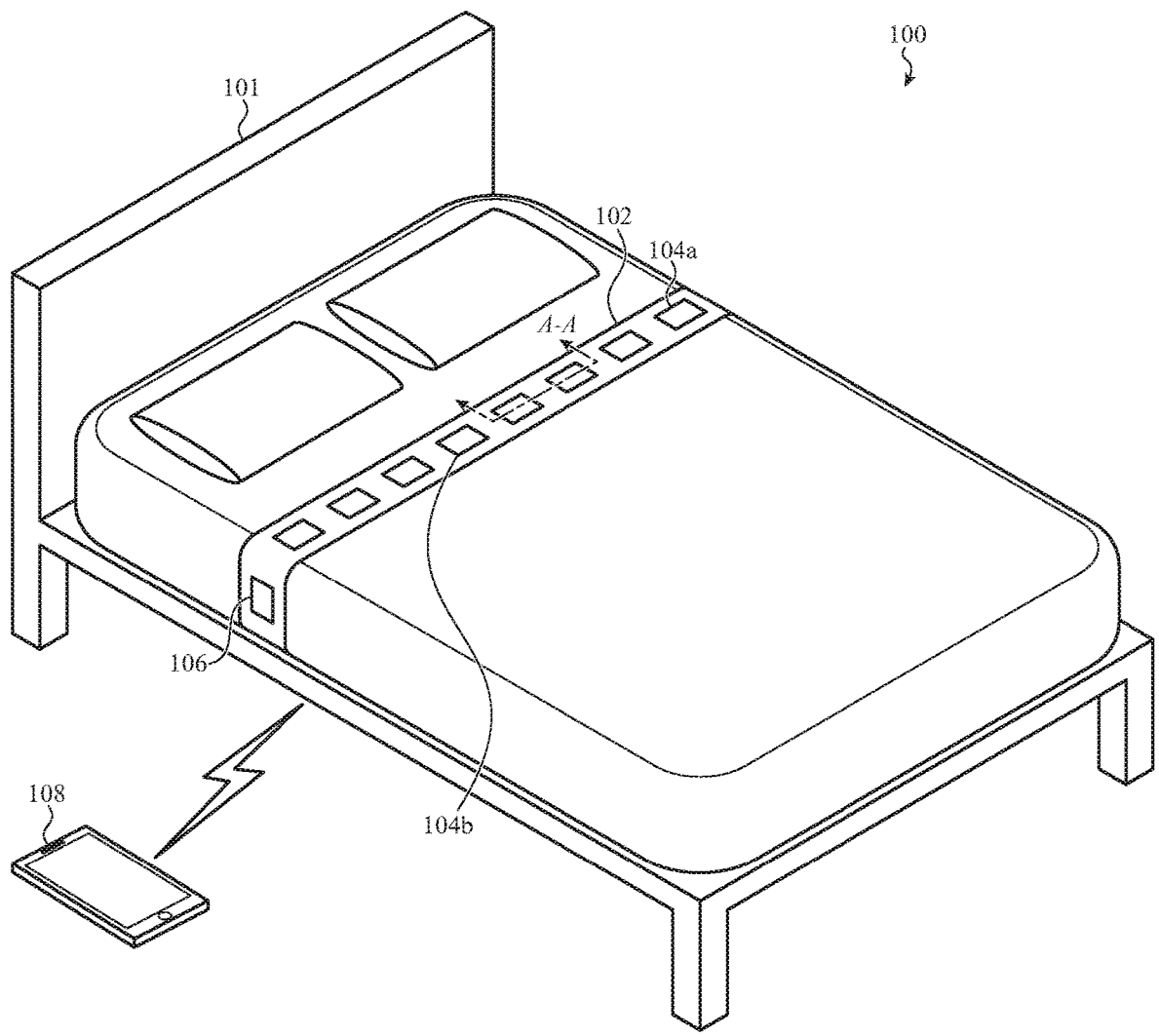
FIG. 1 shows an example of a temperature sensing device placed on, or integrated into, a bed.

It should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Embodiments disclosed herein are directed to a temperature sensing device for tracking the temperature of a user over an extended period of time. The temperature sensing device can include a flexible housing that encloses one or more temperature sensors arranged in an array or other defined configuration. The temperature sensing device can be placed on or integrated with various objects that a user may interact with on a daily basis. For example, the temperature sensing device can be configured as a flexible strip that is configured to be placed on a bed, such as over a mattress, integrated within a sheet, a pad, or the like. The flexible strip can position multiple temperature sensors across the bed such that at least one of the temperature sensors is positioned under a user when the user is lying on the bed. In this regard, the temperature sensing device can measure a temperature of the user over an extended period of time, such as while the user is sleeping. Obtaining temperature measurements of the user over the extended period of time may result in more accurate or substantive temperature data for the user as compared to a user taking a single temperature measurement using a thermometer or other device. For example, the extended temperature data can lead to a more accurate basal body temperature (BBT) measurement for the user by averaging or otherwise analyzing temperature periods taken over a sleep period.

Integrating the temperature sensing device with objects that a person routinely interacts with can also facilitate measuring and tracking temperatures for the person on a regular basis. For example, interfacing the temperature sensing device with a bed can allow temperatures for the user to be measured and recorded each night. This regularly tracked temperature data can be used to identify or determine temperature trends such as an increase in temperature due to ovulation. In other cases, regularly tracked temperature data can be used to identify and/or track a fever. In some cases, tracked temperature data can be used to predict future events such as a start date of a next menstrual period, a next ovulation date, when a fever may end, and so on.

The temperature sensing device described herein can be integrated into a variety of devices including bedding as described herein; other furniture such as chairs, couches, seats, and so on; or wearable devices such as smart watches, glasses, jewelry, clothing, and health monitoring devices. Accordingly, the temperature sensing device may need to accommodate or withstand normal movements of a user. For example, the temperature sensing device may need to withstand repeated bending or other deformation due to movements of a user. Further it may be desirable to decrease the size or thickness of the temperature sensing device to minimize impact or discomfort for a user. For example, a user sleeping on a bed tends to be sensitive to objects that are positioned between the user and a mattress. Accordingly, decreasing the thickness of the temperature sensing device may have a significant impact on a user's comfort while they are lying on the temperature sensing device.

A first set of embodiments is directed to a thin film temperature sensing device that can be incorporated into a flexible strip that can be positioned on a mattress. The thin film temperature sensing device can include a substrate formed using a thin sheet that defines a first side and a second side. A temperature sensor can be formed on the substrate by coupling a first conductive material on the substrate, and then patterning or etching the first conductive material into a continuous pattern that extends from a first location on the substrate (which may be referred to as a "first node") to a second location on the substrate (which may be referred to as a "second node"). As used herein the term "coupling" can include processes that are used to attach one material to another material such as attaching a first layer of material to a second layer of material. Coupling processes can include techniques such as bonding, depositing, lamination, passivation, sputtering, lithography, printing, electroplating, or the like, or a combination of these techniques. The continuous pattern can take on a variety of configurations such as a serpentine pattern. The material and pattern of the temperature sensor can be configured such that an electrical characteristic of the temperature sensor, such as resistance, changes in response to a change in temperature of the temperature sensor.

The thin film temperature sensing device can also include conductive traces that are configured to apply an electrical signal to the temperature sensor and detect an effect of the temperature sensor on the electrical signal. For example, as the temperature of the temperature sensor material changes, its electrical resistance may change. This change in electrical resistance may be determined by a sensing circuit using the conductive traces. In order to decrease a thickness of the temperature sensing device, the conductive traces can be formed on the substrate. In some cases, two wire traces can be used in which the two wires both apply the electrical signal to the temperature sensor and detect an effect of the temperature sensor on the electrical signal. In other cases, four wire traces can be used to increase an accuracy of the temperature measurements. For example, a first set of conductive traces can be used to apply an electrical signal to the temperature sensor and a second set of conductive traces can be used to detect an effect of the temperature sensor on the electrical signal. For example, the first set of conductive traces can be used to apply a drive signal to the temperature sensor and the second set of conductive traces can determine a resistance of the temperature sensor based on detecting changes to the drive signal due to the temperature sensor. The first set of conductive traces can include a first trace that is electrically coupled to the first node of the temperature sensor and a second trace that is coupled to the second node of the temperature sensor. The second set of conductive traces can include a third trace that is coupled to the first node of the temperature sensor and a fourth trace that is coupled to the fourth node of the temperature sensor. The traces can be routed across the substrate to a bonding location where they can be coupled to processing circuitry. In some cases, the conductive traces can be coupled to the processing circuitry using an interposer.

In some embodiments, the conductive material used to form the temperature sensor can be the same material that is used to form the conductive traces. In other cases, a first material may be used to form the temperature sensor and a different material may be used to form the conductive traces. For example, it may be desirable to form the temperature sensor using a platinum or nickel material due to their electrical changes in response to changes in temperature. However, these materials may be expensive and/or subject to cracking when bent. In this regard, platinum or nickel may be used as the conductive material for the temperature sensor and a different material that is less expensive and/or can withstand greater deformation can be used for the trace material. For example, the traces can be formed from a silver or copper material. Accordingly, a first conductive material may be used to form the temperature sensor on the substrate and a second conductive material that is different from the first conductive material can be used to form the traces.

In some cases, a stiffener can be coupled to the substrate in the region of the temperature sensor. The stiffener can decrease flexing or deformation of the temperature sensing device in the region of the temperature sensor while allowing other portions of the temperature sensing device to flex a greater amount. The stiffener may reduce stress or deformation on the temperature sensor while allowing other portions of the temperature sensing device to remain flexible. Accordingly, when integrated into a temperature sensing device such as a flexible bed strip, the thin film temperature sensing device may be able to conform to the shape of the bed and/or user lying on the bed while reducing stress on the temperature sensor. Further, forming the temperature sensor and traces on a flexible substrate may reduce the size (thickness) of the temperature sensing device.

The thin film temperature sensing device can also include a cover layer that is coupled with the substrate to cover and/or seal the temperature sensor and electrical traces. In this regard the temperature sensor and/or electrical traces are sealed between the substrate and the cover layer. In some cases, the substrate and cover layer materials may resist water penetration to protect the temperature sensors and/or electrical traces from moisture, damage, or other contaminants.

In some embodiments, the temperature sensing device can include multiple temperature sensors coupled to a single substrate layer. The multiple temperature sensors can each include one or more sets of traces that electrically couple the temperature sensors to one or more processing circuits. The temperature sensors can form an array that is used to sense temperatures at different locations of the temperature sensing device. For example, these different locations can correspond to different locations in a temperature sensing device such as a temperature sensing strip for placement on a bed.

Another set of embodiments is directed to an embedded temperature sensing device that can be incorporated into a temperature sensing device such as those described herein. The embedded temperature sensing device can include a flexible substrate having a first side and a second side. A temperature sensor, and in some cases one or more traces, such as those described herein can be located on the first side of the substrate. The substrate can also include one or more vias that connect the temperature sensor and/or traces located on the first side to traces and other electrical elements that are located on the second side of the substrate. The substrate can also include one or more electrical interconnects located on the first side of the substrate, where the electrical interconnects are configured to electrically couple the temperature sensor to control circuitry using traces that are located on both the first and second sides of the flexible substrate. In this way, an interposer can be embedded or integrated with the temperature sensing device such that these components are coupled to the same base substrate, which allows direct connection of the temperature sensing device to processing circuitry. Such temperature sensing devices are referred to herein as embedded temperature sensing devices.

The embedded temperature sensing device can be formed by performing one or more processes on a material stack. In some cases, the material stack can include a flexible substrate layer such as a polyimide material that has a first side and a second side. A first conductive material that is used to create the temperature sensors can be coupled to the first side of the polyimide material to form a first conductive layer. A second conductive material that is used to create one or more electrical traces on the first side of the material stack can be coupled to the first conductive material to form a second conductive layer. A third conductive material that is used to create one or more electrical traces on the second side of the material stack can be coupled to the second side of the polyimide material to form a third conductive layer. One or more temperature sensors can be formed in the stack of material by etching, forming vias, and laminating the resulting structure. In this regard, a temperature sensing device comprising multiple temperature sensors along with traces and supporting circuitry can be formed on the flexible substrate. The temperature sensing device can be integrated into various temperature sensing devices such as a flexible strip that is configured for placement on a bed.

In some cases, stiffeners can be coupled to the embedded temperature sensing device in the region of the temperature sensors. The stiffeners can decrease flexing or deformation of the temperature sensing device in the region of the temperature sensors while allowing other portions of the temperature sensing device to flex a greater amount. The stiffeners may reduce stress or deformation on the temperature sensors while allowing other portions of the temperature sensing device to remain flexible. Accordingly, when integrated into a temperature sensing device, such as a flexible bed strip, the embedded temperature sensing device may be able to conform to the shape of the bed and/or user lying on the bed while reducing stress on the temperature sensors. Further, forming the temperature sensors and traces on a flexible substrate may reduce the size (thickness) of the temperature sensing device.

These and other embodiments are discussed below with reference to FIGS. 1-12. However, those skilled in the art will readily appreciate that the detailed description given herein with respect to these Figures is for explanatory purposes only and should not be construed as limiting.

FIG. 1 shows an example of a temperature sensing system 100 having at least a portion that can be placed on, or integrated with, a bed 101 and used to measure a temperature of a user when they are lying or otherwise positioned on the bed 101. The temperature sensing system 100 can include a temperature sensing device 102 that is positioned on the bed 101. The temperature sensing device 102 can be configured as an array of temperature sensors that include multiple temperature sensors 104 that are each configured to output an electrical signal that is indicative of a temperature of a user. The temperature sensing device 102 can also include a processing circuit 106 that is electrically coupled to the temperature sensors 104 and configured to determine a temperature of the user from the electrical signal.

In some embodiments, the temperature sensing device 102 can include a flexible strip, mat, or band that is configured to be placed across a width of the bed 101. In some cases, the temperature sensing device 102 can be integrated into a bed sheet, a blanket, the mattress, a mattress pad, or the like. In some examples, the temperature sensing device 102 can be integrated into other objects such as couches, chairs, rugs, or floors. In other cases, the temperature sensing device 102 could be worn or attached to the user such as being integrated into clothing, or other wearable items. The temperature sensing device 102 can be placed on the bed 101 such that one or more temperature sensors 104 are located under a core portion (e.g., a chest, a torso, etc.) of the user. The temperature sensors 104 can be positioned along the strip, and spaced relative to each other, such that at least one temperature sensor 104 is likely to be completely positioned under the user. In other cases, the temperature sensors 104 can be positioned along the strip and spaced from each other such that multiple temperature sensors 104 are likely to be positioned under the user.

In some embodiments, the temperature sensing device 102 can include a one-dimensional array of temperature sensors as shown in FIG. 1, where multiple temperature sensors 104 are arranged in a single line. For example, the temperature sensors in the array of temperature sensors can be spaced apart from each other along a first dimension of the temperature sensing device 102, such as a first dimension spanning a width of the bed. This first dimension can be longer than a second dimension of the temperature sensing device 102, such as a second dimension that extends along a length of the bed, which is orthogonal to the first dimension.

In other cases, the temperature sensing device 102 can include a two-dimensional array of temperature sensors, where multiple temperature sensors 104 extend in at least two directions. The two-dimensional array can include temperature sensors 104 that are positioned in a variety of configurations such as square, rectangular, circular, or to correspond to the shape of a user. For example, the temperature sensing device 102 can be configured to correspond to the shape of a torso section of the user when the user is lying on their back, side, or front. In this regard, the location of temperature sensors 104 relative to a user may be assumed based on their location within the array and/or based on temperature outputs from each temperature sensor 104. For example, if the user is lying on their back over the temperature sensing device 102, temperature measurements from each temperature sensor 104 can be compared to determine a user's position relative to the temperature sensing device 102. Further, in some cases, this comparison may be used to determine a location of specific temperature sensors 104 relative to the user, for example, that a temperature sensor 104 located centrally within the array of temperature sensors 104 is located under or near the spine of the user. Regardless of whether the temperature sensing device 102 is configured with a one-dimensional array, two-dimensional array, or other configuration of temperature sensors, the temperature sensing device 102 may be positioned on, or integrated into, the top surface of the bed 101.

In some cases, the size of the temperature sensing device 102 can be configured to accommodate different numbers of people lying on a bed and/or different sized beds. The temperature sensing device 102 may be wide enough to accommodate a single user, such that at least one or more temperature sensors 104 are positioned under the user as he or she lays on the bed. In some examples, the temperature sensing device 102 can be configured to extend across a width of the bed, such that temperature sensors 104 span the entire width of the bed. In other cases, the temperature sensing device 102 can be configured to distinguish one user from another user and/or operate the temperature sensors in different sets for different users.

The temperature sensors 104 can be configured to detect a temperature of the user and/or surrounding environment and output a signal indicative of the detected temperature. In some cases, each temperature sensor 104 outputs a signal to the processing circuit, which determines a measured temperature and uniquely identifies the temperature sensor 104 and/or a position of the temperature sensor in the temperature sensing device 102. For example, a first temperature sensor 104a can output a temperature measurement signal along with a unique identifier that indicates that it is the first temperature sensor 104 in the array. Similarly, a second temperature sensor 104b can output a temperature measurement signal along with a unique identifier that indicates that it is the fifth temperature sensor 104 in the array. Accordingly, the temperature sensing device 102 can output multiple temperature measurements that correspond to different temperature sensors 104 within the array. In some cases, the temperature sensing device 102 can output multiple temperature sensor signals and each signal corresponds to a different temperature sensor 104. In other cases, the array can output a single analog or digital signal that contains temperature measurements for each temperature sensor 104 in the array. For example, temperature measurements for all of the temperature sensors 104 can be read out in a predetermined sequence, with positions in the sequence identifying particular temperature sensors 104 and/or their positions within the temperature sensing device 102.

The processing circuit 106 can also be configured to collect outputs from the temperature sensors 104 and communicate them to one or more peripheral devices for processing and/or displaying temperature data to the user. The processing circuit 106 can include a processor or controller for acquiring temperature signals from the temperature sensors 104, which can be analog or digital signals. The processing circuit 106 can process, analyze, and/or digitize the temperature signals before transmitting them to one or more peripheral devices such as the electronic device 108. In some cases, this includes filtering the temperature signals, associating temperature data with a time stamp, identifying which temperature sensor 104 each temperature signal corresponds to, and so on. In some cases, the processing circuit 106 can combine individual temp measurements into a single measurement (e.g., by averaging all of the temperature measurements received from the temperature sensors 104, or all temperature measurements within a range of temperature measurements, or all temperature measurements determined to be from under a user). In some cases, the processing circuit 106 can include a power source such as a battery and/or plug in power source.

The electronic device 108 can be a standalone device such as a smartphone, a tablet, a laptop, a computer, a virtual assistant, a wearable device such as a watch, a wristband, or a physiological monitoring device, or other electronic device. In some cases, the electronic device 108 can be integrated into the temperature sensing device 102. For example, the electronic device 108 can include a user interface that is integrated with the processing circuit 106. The electronic device 108 can communicate with the temperature sensing device 102 (e.g., processing circuit 106) using wired or wireless connections. The electronic device 108 can be configured to receive temperature measurements from the temperature sensing device 102, analyze and/or process the temperature data, and output information to a user. For example, the electronic device 108 can be configured to determine a temperature of a user for each use. The electronic device 108 can use this temperature information in a variety of ways such as to estimate a day that ovulation will occur for a user, to predict a start date of a next menstrual cycle, to predict an ovulation date in a subsequent menstrual cycle, to determine and/or track a fever, and so on.

In some cases, the electronic device 108 can track temperature information of the user to identify fevers, illness, or other events associated with other cycles, conditions, ailments, or diseases. In some examples, the electronic device 108 can use the temperature data when evaluating a sleep quality of the user. In other cases, the temperature sensing device 102 can be used to detect the presence of the user in the bed. For example, an increase in temperature detected by one or more temperature sensors 104 in the array could be used to determine that a user is positioned in the bed above one or more of the temperature sensors 104. In further examples, the electronic device 108 can be used to monitor temperature information of the user for other purposes, such as thermal management. For example, the electronic device 108 can be configured to interface with a temperature control system for the surrounding environment, and the temperature of a room can be controlled based on the user's body temperature.

In some embodiments, the temperature sensing system 100 can include additional sensors and/or receive data from other external sensors that can be used in conjunction with the temperature sensing device data. For example, the temperature sensing device 102 can include touch, force, or pressure sensors that identify a position of the user relative to the array of temperature sensors 104. Such position data can be used to identify temperature sensors that are positioned under the user, such that temperature measurements from these sensors can be used while temperature measurements from other sensors that are not positioned under the user can be discarded or ignored. In some cases, outputs from touch, force, and/or pressure sensors could be used to determine if a user is contacting a specific temperature sensor 104 or a degree of contact with a specific temperature sensor 104. In further examples, the temperature sensing system 100 can include one or more sensors to track heart rate, respiration, blood pressure, humidity data, body weight, or other physiological parameters associated with the user.

In some cases, the temperature sensors 104 can be used to determine a position of the user on the bed 101 and/or relative to the temperature sensing device 102. For example, temperature data from the temperature sensors 104 can be used to determine where the user is positioned on the temperature sensing device 102. In some cases, temperature data from the temperature sensors 104 can be used to determine a posture of the user in the bed 101, such as whether the user is lying on their back, side, or stomach.

In some cases, one or more position sensors can be used to sense a location of the user on the bed and/or relative to temperature sensors in the array. Position sensor data can be used to determine the use period for the first and second temperature sensors. For example, if the position sensors detect that the user is positioned over the first and second temperature sensors for the defined duration, this location data could be used in determining the use period for the array of temperature sensors.

Additionally or alternatively, the temperature sensing device and/or one or more other sensors such as position sensors can be used to determine whether multiple people and/or animals are located in the bed 101. For example, the temperature data from the temperature sensors 104 can be analyzed to determine if there are more than one increased thermal regions which can indicate multiple bodies are on the bed 101. The temperature data can be analyzed along with other sensor data such as position sensor data.

The temperature sensing system 100 can be implemented in a variety of ways. For example, in addition or alternatively to the bed sensor described herein, the temperature sensing system 100 can be implemented in wearable devices such as a smart watch, a wearable health tracking monitor, in clothing worn by the user, head bands, glasses, or a combination thereof. Data from these devices can be used individually or in conjunction with the bed-based sensor for tracking menstrual cycles of a user as described herein.

Figure 2:
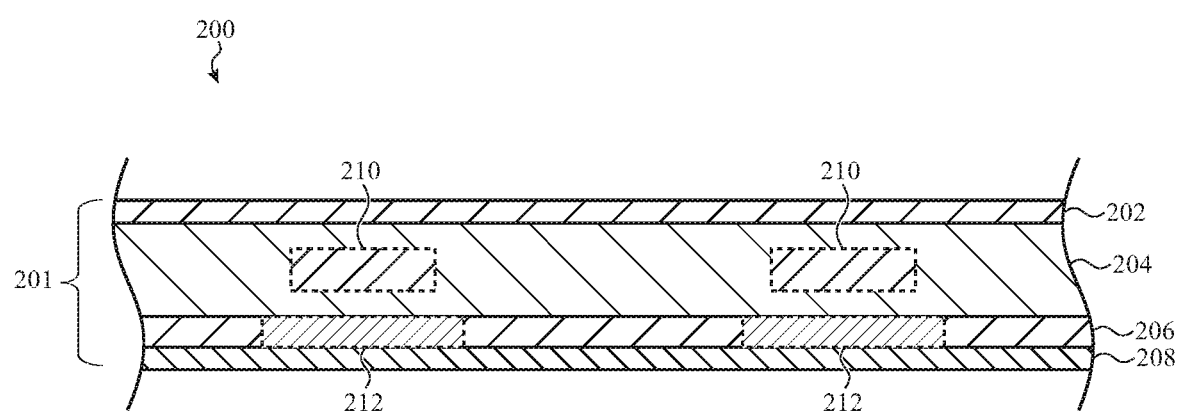
FIG. 2 shows a cross-sectional view of an example temperature sensing device.

FIG. 2 shows a cross-sectional view of an example temperature sensing device 200. In some cases, the cross-section of the temperature sensing device 200 may be taken along section line A-A shown in FIG. 1. The temperature sensing device 200 can be an example of the temperature sensing devices described herein such as temperature sensing device 102. The temperature sensing device 200 can include a housing 201 containing a sensor stack 204. The housing can be defined by a top layer 202 and a bottom layer 208. The temperature sensor stack 204 can be positioned within the housing 201, and the temperature sensor stack 204 can include one or more temperature sensors 210, which can be examples of the temperature sensors described herein such as temperature sensors 104. The temperature sensor stack 204 can also include one or more layers of materials that are used to form the temperature sensors 210 and electrical traces, substrates, encapsulants, and the like, as described herein. The temperature sensing device 200 can also include a reinforcing layer 206 that includes one or more stiffeners 212, each of which is positioned in a region of one or more of the temperature sensors 210.

In some embodiments, the temperature sensor stack 204 can include an array of temperature sensors 210. The sensor stack 204 can include multiple layers that form a flexible structure that includes the temperatures sensors 210 along with other components such as electrical traces which are described in greater detail in reference to FIGS. 3-12. The temperature sensors can include one or more of resistance temperature detectors (RTD), negative temperature coefficient (NTC) detectors, thermocouples, semi-conductor temperature detectors, or any other suitable temperature detectors, or any combination thereof. In some cases, the temperature sensors 210 can be configured as single heat flux temperature sensors and/or dual heat flux temperature sensors such as four-point temperature sensors that can be operated to estimate a subsurface temperature of a user.

In some embodiments, the temperature sensing device 200 can include one or more layers that define the temperature sensor stack 204. For example, the top layer 202 can be formed from a first material, which forms a cover layer of the temperature sensing device 200. The top layer 202, alone or in combination with other layers or components, can seal the sensor stack 204 from the surrounding environment to protect it from physical damage, moisture, or other environment factors. The top layer 202 can be positioned between the temperature sensor stack 204 and a user. In some cases, the top layer 202 can be formed from a flexible material and configured to transfer heat from a user to the temperature sensors 210. For example, the top layer 202 may be relatively thin to decrease its resistance to heat transfer from the user and to the temperature sensors 210. The top layer 202 can be formed from one or more materials that include fabrics, polymers, or any other flexible material that is used to provide an interface between the top sensor stack 204 and the user. The sensor stack 204 can also include one or more flexible materials. The flexible materials can be coupled with the temperature sensors 210 and allow the sensor stack 204 to bend, flex, or otherwise deform, to allow the temperature sensors 210 to move relative to each other.

In additional examples, temperature sensing device 200 can include a bottom layer 208, which can be configured to couple the temperature sensing device 200 with a bed. For example the bottom layer 208 can be formed from a high friction material, an adhesive material, a hook-and-loop fastener, or any other suitable material that can removably couple the temperature sensing device 200 to a bed. In this regard, the temperature sensing device 200 can be removed and reattached to the bed. The bottom layer 208 of the sensor stack 204 can form a flexible array that can be positioned on a bed or other surface and conform to the unique contours of an individual user such as the shape of a user's back, side, or front as they lie on the bed. In some cases, the temperature sensing device 200 can be configured to attach to other objects such as watches, clothing, headbands, wristbands, chairs, and so on.

In some embodiments, the temperature sensing device 200 can include one or more stiffeners 212 that are positioned between the temperature sensors 210 and bottom layer 208. The stiffeners 212 can protect the temperature sensors 210 from mechanical damage such as detachment or cracking of the sensors and/or electrical contacts when the sensor stack flexes to conform to the shape of a user. The stiffeners 212 can also aid heat transfer between a user and the temperature sensors 210, and/or help develop a stable reading of a body temperature of a user. The stiffeners 212 can each couple to the temperature sensor stack in a region of the temperature sensors. In this regard, the stiffeners may increase a rigidity of the temperature sensing device 200 and/or sensor stack 204 in the region of the temperature sensors 210, while allowing the temperature sensing device 200 and/or sensor stack 204 to remain flexible in other regions.

Figure 3:
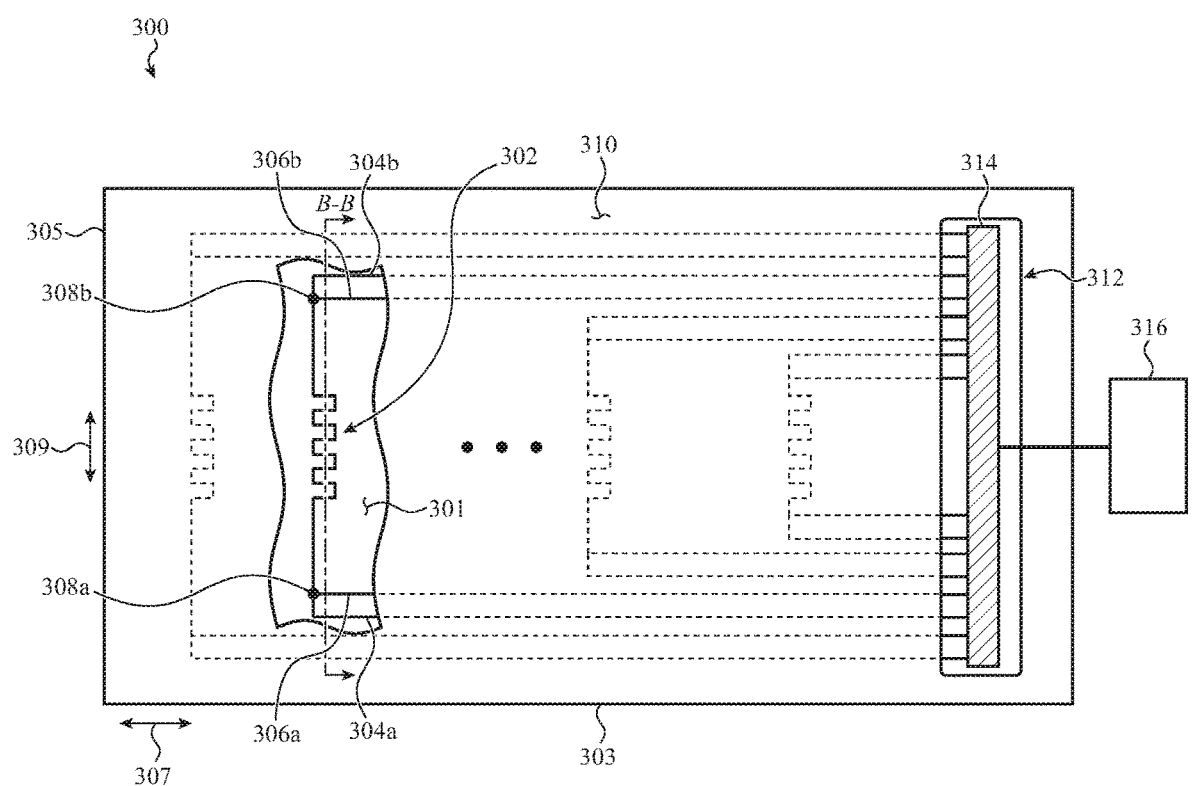
FIG. 3 shows a plan view of an example thin film temperature sensing device.

FIG. 3 shows a plan view of an example thin film temperature sensing device 300. The temperature sensing device 300 can include multiple temperature sensors 302, one of which is labeled for clarity. The temperature sensors 302 can be an example of the temperature sensors as described herein such as temperatures sensors 104 and 210. The temperature sensing device 300 can also include traces 304 and 306. The conductive traces 304 and 306 can be examples of the conductive traces described herein. The temperature sensing device 300 can also include a cover layer 310, an opening 312 in the cover layer 310, an interposer interface 314, and a processing circuit 316.

In some embodiments, the temperature sensor 302 can be coupled to a flexible substrate 301. The flexible substrate 301 can be a thin sheet or film and formed from an electrically insulating material. The flexible substrate 301 can be formed in an elongated sheet that has a length 303 extending along a first dimension 307 and a width 305 extending along a second dimension 309. In some cases the sheet can be rectangular and the length 303 can be orthogonal to and longer than the width 305. For example, the length 303 of the temperature sensing device 300 can be configured to extend across a mattress, or portion of a mattress. Multiple temperature sensors 302 can be spaced along the width 305 of the temperature sensing device 300. In some cases, the temperature sensors 302 can spaced at regular intervals, which can be configured such that one or more temperature sensors are positioned under or against a user when the strip is integrated into a bed or other object. The width 305 may be based on the number of traces, such as traces 304 and 306 that are included in the temperature sensing device 300. In some cases, the substrate can include a polyethylene terephthalate (PET) material, or any other suitable material.

The temperature sensor 302 can include a conductive material that forms a continuous pattern on the substrate that extends from a first node 308a to a second node 308b. The pattern can include a repeating structure such as a square, sine wave, or other form of serpentine pattern, or any other suitable continuous form. In other cases, the pattern of the temperature sensor 302 can be any defined shape that includes non-repeating forms, repeating forms, or any combination thereof. The pattern, the conductive material, and/or the dimensions used to form the temperature sensor 302 may be configured such that the electrical properties of the temperature sensor 302 change in response to changes in temperature. For example, as the temperature of the temperature sensor 302 changes, the electrical resistance of the temperature sensor 302 can change in a predictable and/or repeatable way. Accordingly, by monitoring the changes in an electrical signal applied of the temperature sensor 302, a temperature of an object contacting the temperature sensing device in the region of the temperature sensor 302 can be detected. In some examples, the conductive material used to form the temperature sensor 302 can include platinum, nickel, copper, silver, or other suitable material, or a combination thereof.

The temperature sensing device 300 can include a first set of conductive traces 304 that are formed on the substrate 301. The first set of conductive traces 304 can include a first trace 304a that is electrically coupled to the first node 308a and a second trace 304b that is electrically coupled to the second node 308b. The first set of conductive traces 304 can be formed from one of more conductive materials, which can be the same or different material as the temperature sensor 302. In some cases, the first set of conductive traces 304 can be formed from platinum, nickel, copper, silver, or other suitable material, or a combination thereof. The first set of conductive traces 304 can electrically couple the temperature sensor 302 to the processing circuit 316. In this regard, the first set of conductive traces 304 can be operative to apply an electrical signal from the processing circuit 316 across the temperature sensor 302. In some cases, a two lead system may be employed where the first set of conductive traces 304 is used both to apply the electrical signal to the temperature sensor 302 and detect an effect of the temperature sensor on the electrical signal; for example, a change in resistance, current, or voltage that can be correlated to a temperature of the temperature sensor 302 by the processing circuit 316 or other device.

In some cases a four lead system may be employed to increase the accuracy of temperature measurements produced by the temperature sensor 302. For example, the first set of conductive traces 304 can be used to apply an electrical signal to the temperature sensor 302 and the second set of conductive traces 306 can be used to detect an effect of the temperature sensor on the electrical signal. The second set of conductive traces 306 can include a third conductive trace 306a that is coupled to the first node 308a and a fourth conductive trace 306b that is coupled to the second node 308b. The second set of conductive traces 306 can be formed from one of more conductive materials, which can be the same or different material as the first set of conductive traces 304. In some embodiments, a first temperate sensor may be monitored using a four lead sensor, and other sensors may be monitored using a three lead sensor, in a 3n+1 configuration with the four lead sensor. In some cases, the conductive traces 304 and 306 can be formed from a material that can undergo greater strain than the temperature sensor 302 material such that portions of the temperature sensing device 300 that include the traces 304 and 306 can undergo greater amounts of deformation than the temperature sensor 302 regions. The second set of conductive traces 306 can electrically couple the temperature sensor 302 to the processing circuit 316. In this regard, the second set of conductive traces 306 can be operative to detect an electrical signal applied to the temperature sensor 302 by the processing circuit 316.

The first and second sets of conductive traces 304 and 306 can be routed along various paths on the flexible substrate 301. For example, the first and second sets of conductive traces 304 and 306 can be routed across the substrate 301 from the temperature sensors 302 to a location on the substrate 301 where they can be coupled to the processing circuit 316.

The temperature sensing device 300 can also include a cover layer 310 that is coupled to the substrate 301 and positioned over the temperature sensor 302 and the first and second sets of conductive traces 304 and 306. The cover layer 310 can be bonded to the flexible substrate 301 and/or one or more components that are formed on the flexible substrate 301 such as the temperature sensor 302 and the first and second sets of conductive traces 304 and 306. In this regard, the cover layer 310 may protect electrical components positioned on the flexible substrate from water, debris, or other contaminants. Additionally or alternatively, the flexible substrate 301 and/or the cover layer 310 can reinforce the electrical components such as the temperature sensor 302 and traces to protect these components from mechanical damage. In some embodiments, the cover layer 310 can have one or more openings positioned at different locations in the cover layer 310. For example, opening 312 can be positioned such that terminal ends of the first and second sets of conductive traces 304 and 306 are exposed for coupling the temperature sensing device 300 to one or more other components such as the processing circuit 316. In some cases, an end of the cover layer 310 can be shorter than the substrate, such that the end of the cover layer 310 is offset from the end of the substrate 301 and leaves an exposed portion of the substrate 301 where the conductive traces 304 and 306 can terminate and be exposed to couple with other electrical components such as the interposer interface 314.

In some cases, the interposer interface 314 can be used to couple the temperature sensing device 300 to the processing circuit 316. The interposer interface 314 can be a distinct component from the temperature sensing device 300 that is coupled to the temperature sensing device 300 to provide electrical interface routing between the temperature sensing device 300 and the processing circuit 316. In some cases, the processing circuit 316 can be implemented as one or more electrical circuit boards such as a flexible circuit board. In other cases, the interposer interface 314 can be integrated with the temperature sensing device 300 and/or processing circuit 316.

The processing circuit 316 can be configured to apply an electrical signal across the conductive material of each temperature sensor 302 using the traces such as the first set of conductive traces 304 or the second set of the conductive traces 306. The processing circuit 316 can also be configured to detect an effect of the temperature sensor on the electrical signal, such as a current or voltage that corresponds to a temperature of the temperature sensor 302. The processing circuit 316 can use traces such as the first set of conductive traces 304 or the second set of the conductive traces 306 to detect electrical signals applied to the temperature sensor 302. In some embodiments, the processing circuit 316 determines a temperature for the temperature sensor 302 using the detected effect of the conductive material on the electrical signal. For example, the processing circuit 316 can correlate a detected electrical response such as a voltage drop, change in current, and so on to a temperature of the temperature sensor 302.

Figure 4:
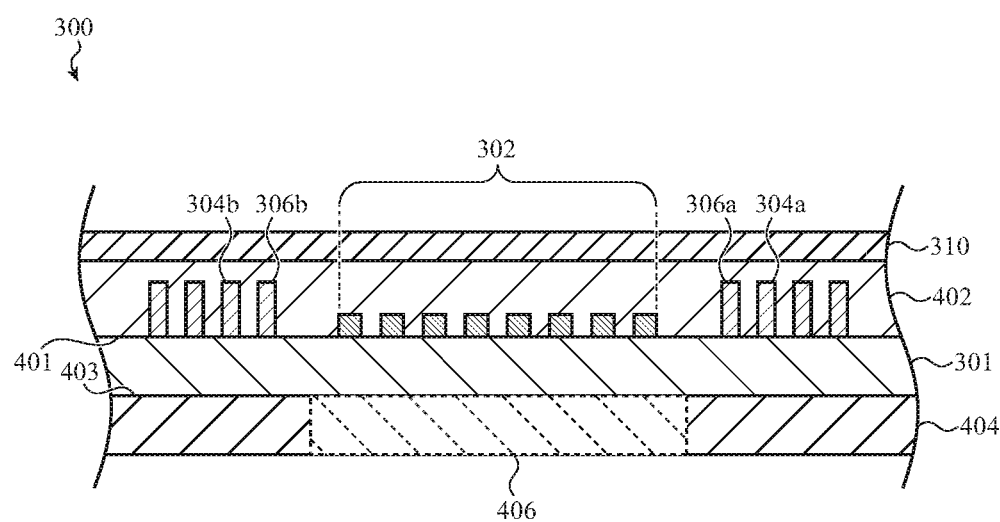
FIG. 4 shows an example cross-sectional view of the thin film temperature sensing device shown in FIG. 3.

FIG. 4 shows an example cross-sectional view of the thin film temperature sensing device 300. The cross-section of the temperature sensing device 300 is taken along section line B-B shown in FIG. 3. The temperature sensing device 300 can include the flexible substrate 301, the temperature sensor 302, the first set of traces 304, the second set of traces 306, and the cover layer 310 described with reference to FIG. 3. The temperature sensing device 300 can also include a coupling material 402, a reinforcing layer 404, and a stiffener 406.

As shown in FIG. 4, the flexible substrate 301 can include a first side 401 and a second side 403. The temperature sensor 302, the first set of conductive traces 304, and the second set of conductive traces 306 can be formed on the first side 401 of the flexible substrate 301. In some cases, the coupling material 402 can couple the cover layer 310 to the flexible substrate 301. The coupling material 402 can be an adhesive material and conform to the surface of the substrate 301 and features formed on the substrate 301. For example, the coupling material 402 can surround the conductive material forming the temperature sensor 302 and/or conductive traces such as the first and second sets of conductive traces 304 and 306. In this regard, the coupling material 402 may form an adhesive layer that couples the cover layer 310 to the flexible substrate 301. The coupling material 402 in combination with the cover layer 310 can form a protective layer(s) over the temperature sensor 302 and traces that can help protect these components from moisture, dust, debris, and other contamination as well as provide mechanical protection to these components. In some embodiments, the coupling material 402 and/or the cover layer 310 can be formed from flexible materials that allow the temperature sensing device 300 to bend and/or otherwise conform to various uneven surfaces, In some embodiments, the stiffener 406 can be coupled to the second side 403 of the flexible substrate 301. The stiffener 406 can be positioned in the region, such as a footprint, of the temperature sensor 302. In some cases, the shape and size of the stiffener 406 can be configured such that it corresponds to a shape and size of the temperature sensor 302. For example, the stiffener 406 may be sized to be the same size as or slightly bigger than the footprint of the temperature sensor 302 such that the edges of the stiffener extend to or past the outer profile of the temperature sensor 302. In other cases, the stiffener 406 can be sized to be smaller than the footprint of the temperature sensor 302 such that the edges of the stiffener do not extend past the outer profile of the temperature sensor 302. The stiffener 406 can be formed from a material that is more rigid than the flexible substrate 301, to increase the bending resistance of the flexible substrate 301 in the region of the temperature sensor 302. In this regard, the temperature sensor 302 may undergo less deformation than other portions of the temperature sensing device 300. Such configuration may protect the temperature sensor 302, such as from cracking or otherwise breaking, as the temperature sensing device 300 deforms to accommodate different surfaces or movements of a user. In some cases, the stiffener 406 can be coupled to the second side of the flexible substrate 301. The stiffener 406 can be located on a reinforcing layer 404 that includes one or more stiffeners corresponding to temperature sensors in the array, and a flexible material that is positioned between different stiffeners. In this regard, the temperature sensing device 300 can be stiffer in the regions of the temperature sensors 302 and remain flexible in other regions. Additionally or alternatively, the size and position of the stiffener can be configured such that a neutral bending plane of the temperature sensor 302 coincides with the temperature sensor layer. In this regard, stress on the temperature sensor 302 due to deformation of the temperature sensor 302 can be reduced.

FIGS. 5A-5D show example processes 500 for forming a thin film temperature sensing device. The processes 500 can be used to manufacture the temperature sensing devices described herein such as temperature sensing device 102, 200, and 300. In some cases, the processes 500 provide alternative methods of manufacturing temperature sensing devices, however, various aspects of the processes 500 can be combined and/or substituted.

Figure 5A:
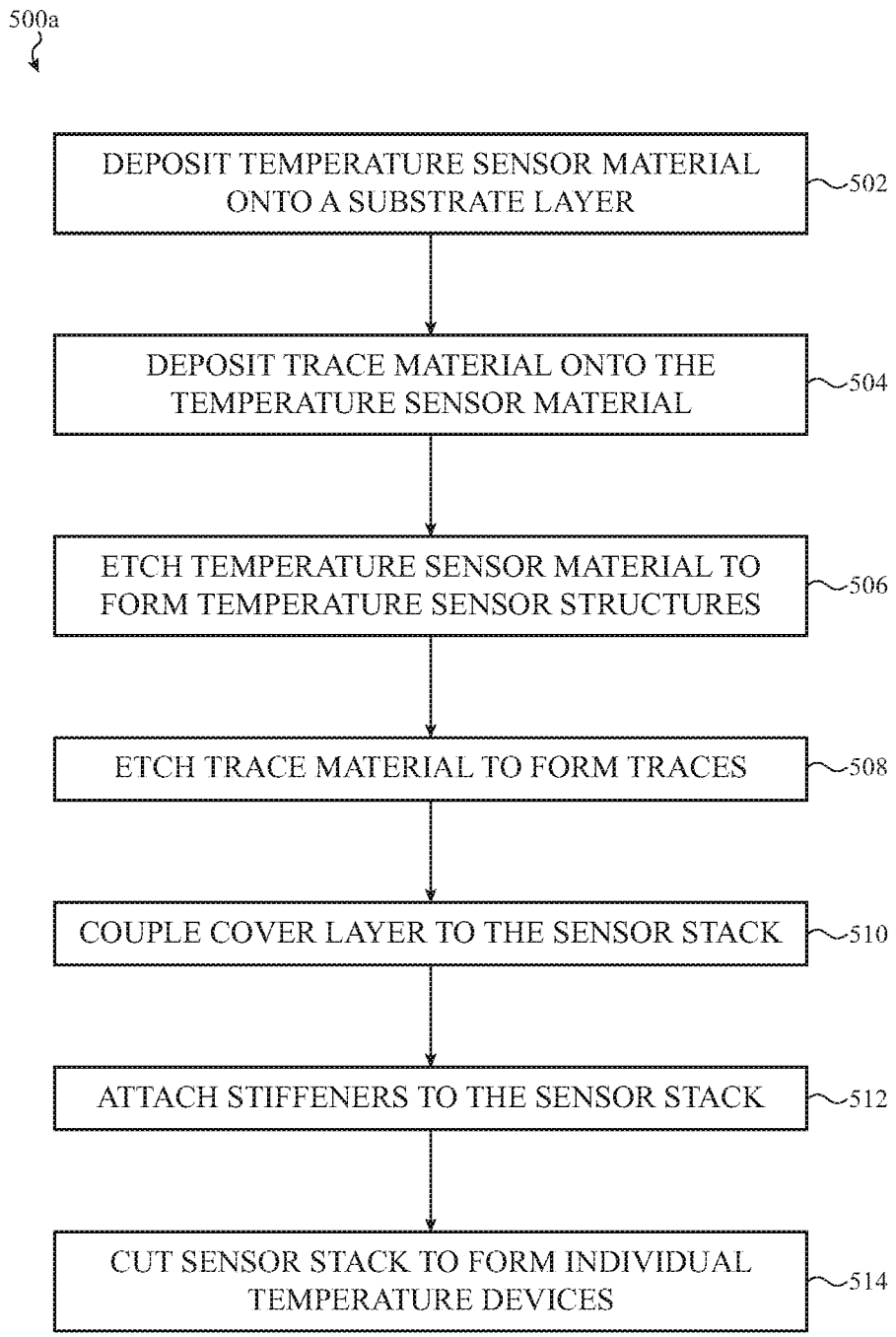
FIGS. 5A-5D show example processes for forming a thin film temperature sensing device.

FIG. 5A shows a first process 500a that can be used to form a temperature sensing device. At 502, the first process 500a can include coupling a first material onto the substrate layer that will be used to form the temperature sensor. The substrate layer can be a flexible substrate layer as described herein and can be a PET material, or other suitable material. The substrate layer can be a sheet such as a rectangular sheet. The first material can be a conductive material such as nickel, platinum, copper, or other suitable material. In some cases, the first material can be deposited over substantially the entire surface of the substrate. For example, the first material may be deposited to form a layer of uniform thickness conductive material that will be further processed at later steps to form the temperature sensors.

In some cases, at step 502, the substrate layer and the first material can be configured such that multiple temperature sensing devices can be formed on a single sheet of substrate and divided into individual temperature sensing devices at a later stage.

At 504, the first process 500a can include coupling a second material onto the first material, where the second material will be used to form the conductive traces. The second material can be selectively applied to the first material though processes that include printing, deposition, masking, or other suitable methods. In this regard, the second material may only be applied to a specific portion of the stack. For example, the second material may be applied as strips that extend between each edge of the substrate and the location where the temperature sensors will be formed. At a later step, these second strips of material can be further processed to form conductive traces from each of the temperature sensors and to an electrical interface such as an interposer interface location on the substrate. The second material may be formed from any suitable conductive material including silver and/or copper.

At 506, the first process 500a can include etching the first temperature sensor material to form the temperature senor structures. For example, the first material can be laser etched to form the temperature sensors, which can include forming multiple continuous patterns, each extending from a first node to a second node, where each pattern corresponds to a temperature sensor on the substrate. This removal process can be performed to only remove material that is needed to form the temperature structures on the substrate. In this regard, the remaining first material may remain coupled to the substrate. Accordingly, after the material removal process at 506, the sensor stack can include the temperature detector patterns formed by removing the first material, and these patterns can be surrounded by the remaining first material that is coupled to the substrate but not used to form the temperature sensors. The remaining first material may be separated from the temperature sensor structures by the removed sections of the first material.

At 508, the first process 500a can include etching the second trace material to form the conductive trace structures on the substrate. In some cases, steps 506 and 508 can be performed as a single process where the first and second materials are etched at the same time. In other cases, the first material can be etched during a different process step from the second material. In some cases, etching the second trace material includes selectively etching only the second trace material, while leaving the first material substantially intact. In other embodiments, etching the second material can also include the first material that underlies the second material being etched to remove portions of both of these materials. The etching can be a process such as laser etching that removes portions of the second material to form the conductive traces. Additionally or alternatively, the etching process can include wet chemical etching, which can use selective chemical etchants. The second material can be selectively processed such that conductive traces are formed between each temperature sensor and an electrical interface on the temperature sensing device. In some cases, steps 506 and 508 can be performed such that the first and second materials are processed to leave an electrical interconnection between the temperature sensors and their respective traces. In other cases, the temperature sensors may be electrically connected to the conductive traces using an additional step that adds an electrical interconnect to connect these components.

At 510, the first process 500a can include coupling a cover layer to the sensor stack to laminate the temperature sensors, conductive traces, and/or other components formed on the substrate between the substrate and the cover layer. In some cases, an adhesive can be used to couple the cover layer to the sensor stack. The adhesive can be a pressure sensitive adhesive, an optically clear adhesive or other suitable material that is applied to the surface of the stack, which can include the temperature sensor structures, the conductive trace structures, and, in some cases, exposed portions of the substrate. In other cases, the first material that was deposited at step 502 and not used to form the temperature sensors may remain on the substrate. In these cases, the adhesive material may be bonded to these portions of the first material to couple the cover layer to the flexible substrate. The adhesive may conform to the surface of the material stack to form a coating over the temperature sensors, conductive traces, and/or other structures coupled to the substrate. The flexible substrate and cover layer stack may protect the conductive materials from environmental factors such as moisture, debris, and/or other contaminants. The flexible substrate and cover layer stack may form a flexible structure that can bend or otherwise conform to a variety of different surface shapes. In some cases, the cover layer can be formed from PET or other suitable materials.

At 512, the first process 500a can include coupling stiffeners to the sensor stack. The stiffeners can be examples of the stiffeners described herein and can be adhesively coupled, or otherwise bonded to a bottom side of the sensor stack, for example, on an opposite side of the flexible substrate from the temperature sensors.

At 514, the first process 500*a* can include cutting the sensor stack to form multiple temperature sensing devices. In some cases, each temperature sensing device can include multiple temperature sensors. For example, the sensor stack can be cut such that each temperature sensing device comprises a strip having a one-dimensional array of temperature sensors extending along a length of the strip.

Figure 5B:
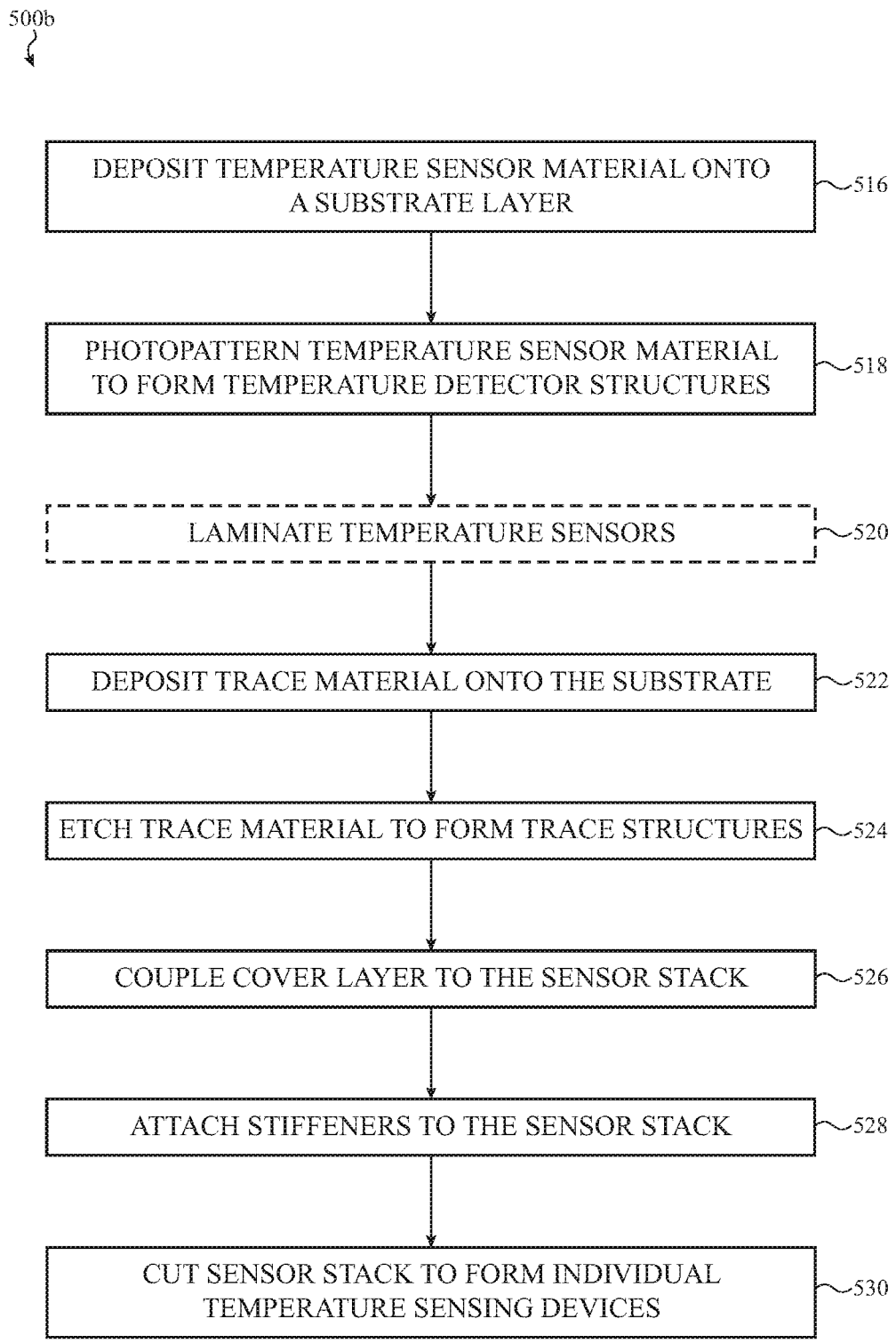

FIG. 5B shows a second process 500*b* that can be used to form a temperature sensing device. At 516, the second process 500*b* includes coupling a first material onto the substrate layer that will be used to form the temperature sensor. Step 516 can be an example of step 502 described in relation to the first process 500*a*.

At 518, the second process 500*b* may include forming the temperature sensors on the substrate by selectively removing portions of the first material. In some embodiments this includes photo patterning and/or etching (e.g., wet chemical etching) the first material to leave only the sections of the first material that are used to form the temperature sensor structures. Accordingly, after step 504, the substrate may contain multiple temperature sensor structures formed from the first material and have the remaining portions of its surface exposed for further processing.

At 520, the second process 500*b* can include laminating the temperature sensors. For example, each temperature sensor formed at step 518 can have a protective coating that covers the temperature sensor.

At 522, the second process 500*b* can include coupling a second material on the substrate that will be used to form the conductive traces on the sensor stack. The second material can be coupled directly to the second substrate. In some cases, coupling the second material to the substrate can include printing processes that are used to selectively deposit the second material onto the substrate. For example, the second material may be applied as strips that extend between each edge of the substrate and the location where the temperature sensors will be formed. At a later step, these second strips of material can be further processed to form conductive traces from each of the temperature sensors and to an electrical interface such as an interposer interface location on the substrate. The second material may be formed from any suitable conductive material including silver and/or copper.

At 524, the second process can include processing the second material to form the conductive trace structures on the sensor stack. The second process can include etching processes such as laser etching that removes portions of the second material to form the conductive traces. The second material can be selectively processed such that conductive traces are formed between each temperature sensor and an electrical interface on the temperature sensing device. In some cases, this process can be performed such that the first and second materials are processed to leave an electrical interconnection between the temperature sensors and their respective traces. In other cases, the temperature sensors may be electrically connected to the conductive traces using additional steps that add an electrical interconnect to connect these components.

At 526, the second process 500*b* can include coupling a cover layer to the sensor stack to laminate the temperature sensors, conductive traces, and/or other components formed on the substrate between the substrate and the cover layer. Step 526 can be an example of step 510 described with reference to the first process 500*a*.

At 528, the second process 500*b* can include coupling stiffeners to the sensor stack. The stiffeners can be examples of the stiffeners described herein and can be adhesively coupled, or otherwise bonded to a bottom side of the sensor stack, for example, on an opposite side of the flexible substrate from the temperature sensors.

At 530, the second process 500*b* can include cutting the sensor stack to form multiple temperature sensing devices. In some cases, each temperature sensing device can include multiple temperature sensors. For example, the sensor stack can be cut such that each temperature sensing device comprises a strip having a one-dimensional array of temperature sensors extending along a length of the strip.

Figure 5C:
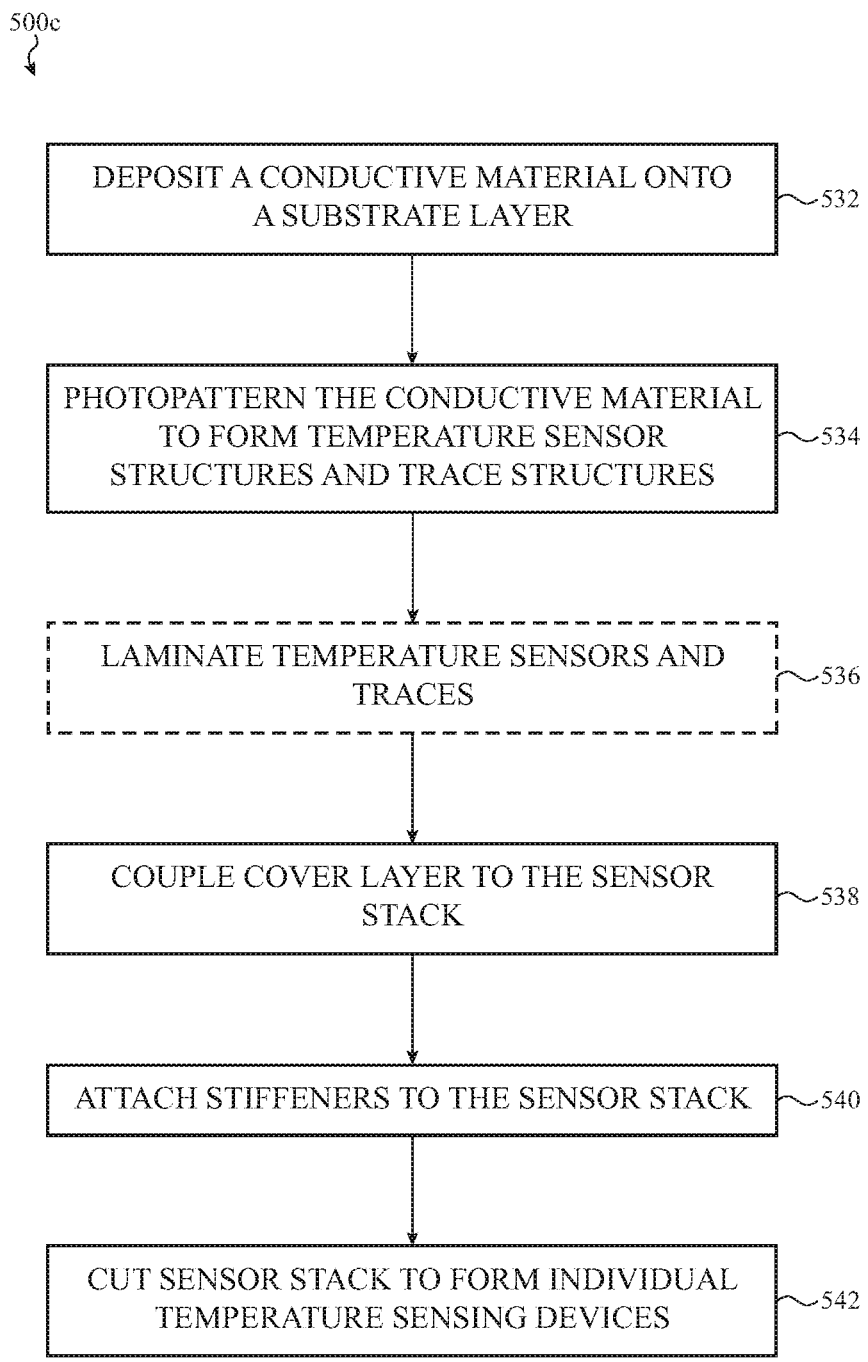

FIG. 5C shows a third process 500*c* that can be used to form a temperature sensing device. At 532, the third process 500*c* can include coupling a first material onto the substrate layer that will be used to form the temperature sensor and the conductive traces. Step 532 can be an example of step 502 described in relation to the first process 500*a*.

At 534, the third process 500*c* can include forming the temperature sensors and conductive traces in the first material. This can include photo patterning the first material to leave only the sections of the first material that are used to form the temperature sensor structures and the conductive traces. Accordingly, after step 534, the substrate may contain multiple temperature sensor structures formed from the first material and each temperature sensor can be electrically coupled to one or more conductive traces that are also formed from the first material.

At 536, the third process 500*c* can include laminating the temperature sensors and conductive traces. For example, each temperature sensor and conductive traces formed at step 536 can have a protective coating that covers these components.

At 538, the third process 500*c* can include coupling a cover layer to the sensor stack to laminate the temperature sensors, conductive traces, and/or other components formed on the substrate between the substrate and the cover layer. Step 538 can be an example of step 510 described with reference to the first process 500*a*.

At 540, the third process 500*c* can include coupling stiffeners to the sensor stack. The stiffeners can be examples of the stiffeners described herein and can be adhesively coupled, or otherwise bonded to a bottom side of the sensor stack, for example, on an opposite side of the flexible substrate from the temperature sensors.

At 542, the third process 500*c* can include cutting the sensor stack to form multiple temperature sensing devices. In some cases, each temperature sensing device can include multiple temperature sensors. For example, the sensor stack can be cut such that each temperature sensing device comprises a strip having a one-dimensional array of temperature sensors extending along a length of the strip.

Figure 5D:
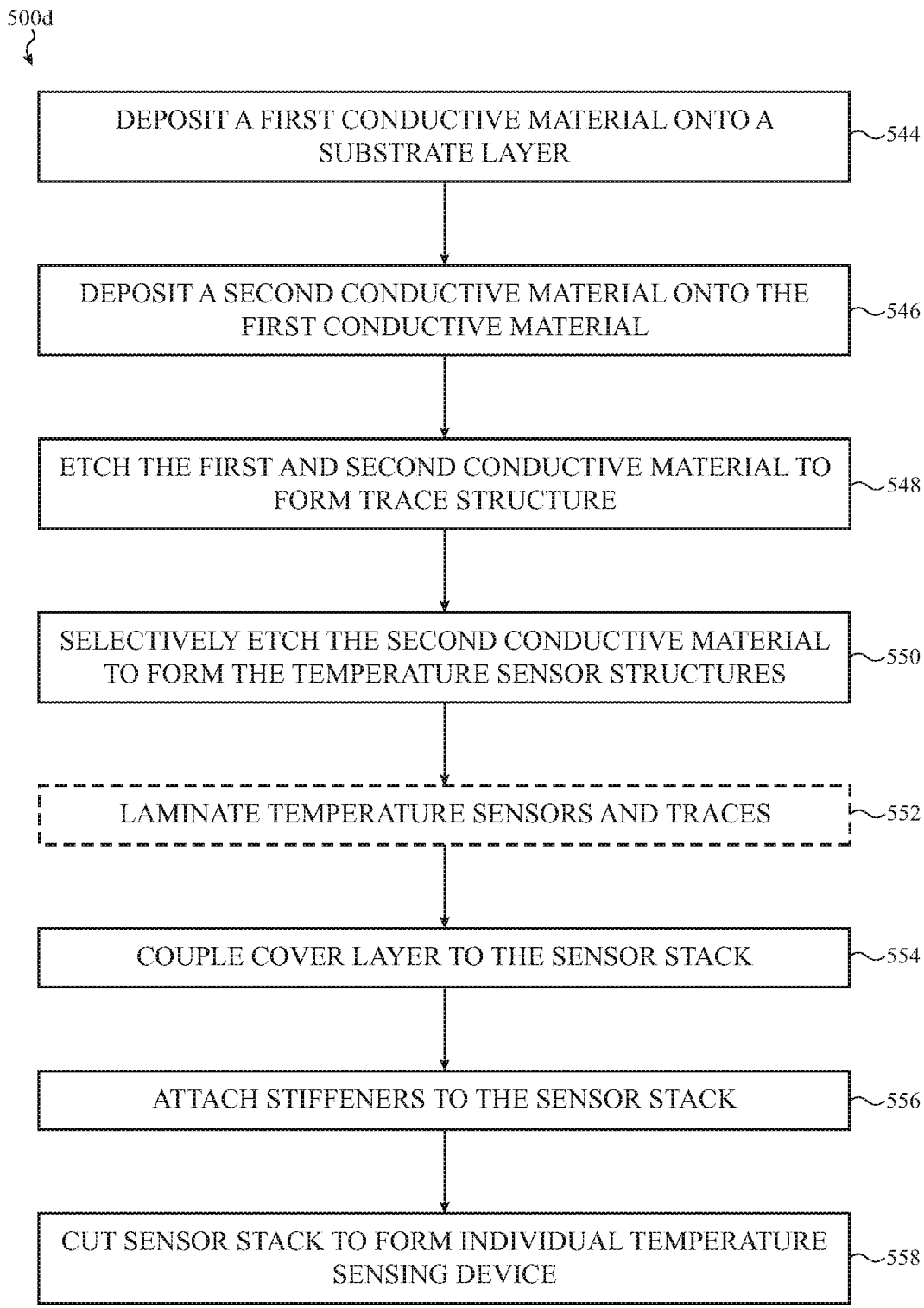

FIG. 5D shows a fourth process 500*d* that can be used to form a temperature sensing device. At 544, the fourth process 500*d* can include coupling a first material onto the substrate layer that will be used to form the temperature sensor. Step 544 can be an example of step 502 described in relation to the first process 500*a*. In some cases, the first material can be a nickel material and the second material can be a copper material.

At 546, the fourth process 500*d* can include coupling a second material onto the first material, where the second material will be used to form the conductive traces. Step 546 can be an example of step 504 described in relation to the first process 500*a*.

At 548, the fourth process 500d can include performing a first material removal process that removes both the first and second materials to form the structure of the temperature sensors and the conductive traces. Accordingly, after step 548, the substrate may contain multiple temperature sensor structures formed from the first material and the second material and each temperature sensor can be electrically coupled to one or more conductive traces that are also formed from the first and second materials.

At, 550, the fourth process 500d can include performing a second material removal process that removes only the second material from the temperature detector structures so that the temperature sensors structures are formed from only the first material. Accordingly, after step 550, the substrate can contain multiple temperature sensor structures formed from the first material.

At 552, the fourth process 500d can include laminating the temperature sensors and conductive traces. For example, each temperature sensor and conductive traces formed at step 550 can have a protective coating that covers these components.

At 554, the fourth process 500d can include coupling a cover layer to the sensor stack to laminate the temperature sensors, conductive traces, and/or other components formed on the substrate between the substrate and the cover layer. Step 554 can be an example of step 510 described with reference to the first process 500a.

At 556, the fourth process 500d can include coupling stiffeners to the sensor stack. The stiffeners can be examples of the stiffeners described herein and can be adhesively coupled, or otherwise bonded to a bottom side of the sensor stack, for example, on an opposite side of the flexible substrate from the temperature sensors.

At 558, the fourth process 500d can include cutting the sensor stack to form multiple temperature sensing devices. In some cases, each temperature sensing device can include multiple temperature sensors. For example, the sensor stack can be cut such that each temperature sensing device comprises a strip having a one-dimensional array of temperature sensors extending along a length of the strip.

Figure 6A:
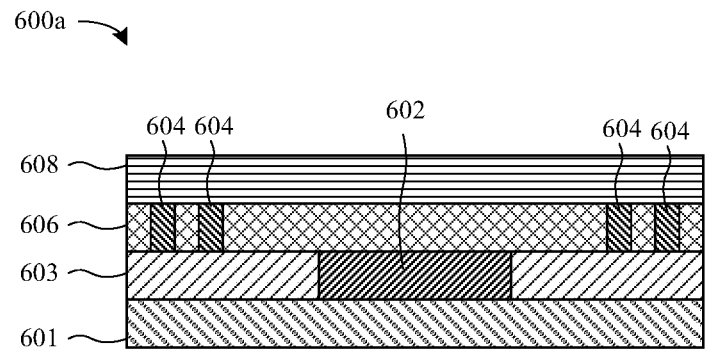
FIGS. 6A-6D show example cross-sectional views of thin-film temperature sensing devices that can be formed using the processes described herein.

FIGS. 6A-6D show example cross-sectional views of thin-film temperature sensing devices 600 that can be formed using the processes discussed in FIGS. 5A-5D. FIG. 6A shows an example temperature sensing device 600a that can be formed by the process described with reference to FIG. 5A. The temperature sensing device 600a can include a flexible substrate 601, a temperature sensor 602 that is formed in a first material 603 layer that is coupled to the flexible substrate 601. The first material layer 603 can be formed from materials described herein such as nickel, platinum, copper or other suitable materials. The temperature sensing device 600a can also include traces 604 that are formed from a second material that is coupled to the first material 603 layer. The second material can include materials described herein that are used to create the conductive traces such as silver, copper, gold, nickel platinum or other suitable materials. In the example temperature sensing device 600a, the temperature sensor 602 can be formed by etching the portions of the first material 603 layer that used to create the temperature sensor 602. The material remaining after the etching process may be left on the flexible substrate 601 to form a layer of first material 603 that surrounds the temperature sensor 602. The etching process may be performed such that the left over first material 603 is electrically isolated from the temperature sensor 602. The temperature sensing device 600a can also include a cover layer 608 that is bonded to the stack using a coupling material 606 as described herein. For example, the cover layer 608 can be a PET material and the coupling material 606 can be an adhesive.

Figure 6B:
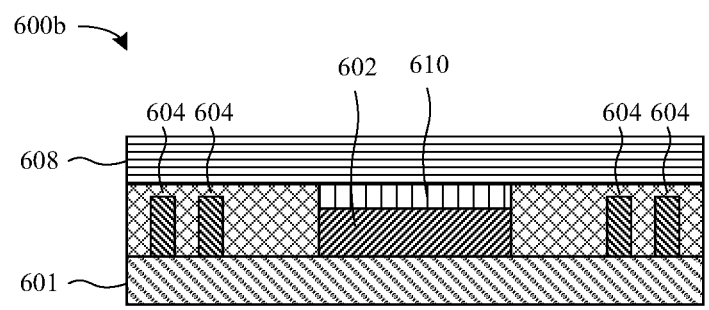

FIG. 6B shows an example temperature sensing device 600b that can be formed by the process described with reference to FIG. 5B. The temperature sensing device 600b can include the flexible substrate 601, the temperature sensor 602, traces 604, a coupling material 606 and a cover layer 608, as described herein. In the example of FIG. 6B, both the temperature sensor 602 and the traces 604 can be positioned on the flexible substrate 601. For example, the temperate sensor 602 can be formed from a first material in a process that removes any of the first material that is not used to form the temperature sensor 602. Accordingly, a second material that is used to form the traces may be coupled directly to the flexible substrate 601. The first and second materials may be different or the same as described herein. In some cases, the temperature sensor 602 can be laminated by a third material 610 as described herein.

Figure 6C:
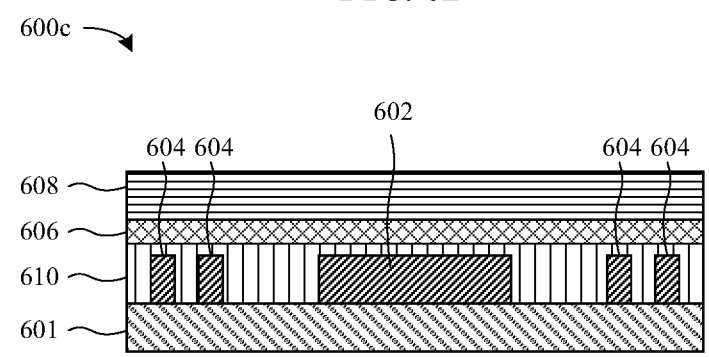

FIG. 6C shows an example temperature sensing device 600c that can be formed by the process described with reference to FIG. 5C. The temperature sensing device 600c can include the flexible substrate 601, the temperature sensor 602, traces 604, a coupling material 606 and a cover layer 608 as described herein. In the example of FIG. 6C, the temperature sensor 602 and the traces 604 can be formed from the same material layer and be covered by a laminate material 610 as described herein.

Figure 6D:
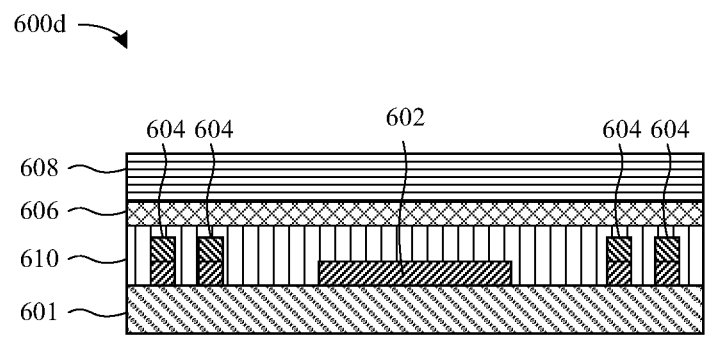

FIG. 6D shows an example temperature sensing device 600d that can be formed by the process described with reference to FIG. 5D. The temperature sensing device 600d can include the flexible substrate 601, the temperature sensor 602, traces 604, a coupling material 606, a cover layer 608, and a laminate material 610 as described herein. In the example of FIG. 6D, the temperature sensor 602 and traces may be formed by depositing a first material onto the flexible substrate and depositing a second material onto the first material. Both the first material and the second material can be conductive. In a first step, both the first and second materials can be etched to form traces 604 that include the two materials and the structure of the temperature sensor 602 (e.g., serpentine pattern). In a second step, the second material can be selectively removed from the region of the temperature sensor 602 such that the temperature sensor 602 is formed from only the first material.

Figure 7:
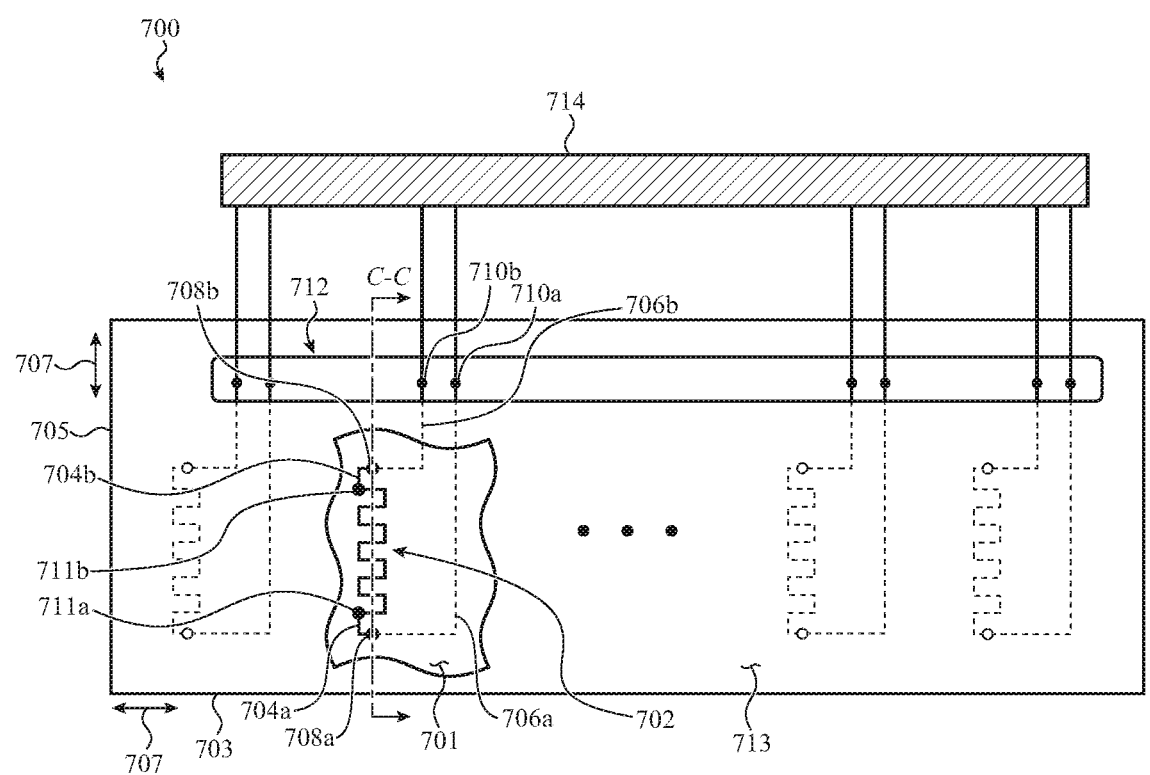
FIG. 7 shows a plan view of an example embedded temperature sensing device.

FIG. 7 shows a plan view of an example of an embedded temperature sensing device 700. The temperature sensing device 700 can be an example of the temperature sensing devices described herein such as temperature sensing devices 102 and 200. The temperature sensing device 700 can include temperature sensors 702, one of which is labeled for clarity, that are formed on a substrate 701. The temperature sensing device 700 can also include traces 704 and 706, electrical interconnects 708, and connection points 710. The conductive traces 304 and 306 can be examples of the conductive traces described herein.

In some embodiments, the temperature sensor 702 can be coupled to a flexible substrate 701. The flexible substrate 701 can be a thin sheet or film and formed from an electrically insulating material. The flexible substrate 701 can be formed in an elongated sheet that has a length 703 extending along a first dimension 707 and a width 705 extending along a second dimension 709. In some cases, the sheet can be rectangular and the length 703 can be orthogonal to and longer than the width 705. For example, the length 703 of the temperature sensing device 700 can be configured to extend across a mattress, or portion of a mattress. Multiple temperature sensors 702 can be spaced along the width 705 of the temperature sensing device 700. In some cases, the temperature sensors 702 can be spaced at regular intervals, which can be configured such that one or more temperature sensors are positioned under or against a user when the strip is integrated into a bed or other object. The width 705 may be based on the number of traces, such as traces 704 and 706 that are included in the temperature sensing device 700. In some cases, the substrate can include a polyimide (PI) material, or any other suitable material.

The temperature sensor 702 can include a conductive material that forms a continuous pattern on the substrate that extends from a first node 711a to a second node 711b. The pattern can include a repeating structure such as a square wave, a sine wave, or any other suitable continuous form. In other cases, the pattern of the temperature sensor 702 can be any defined shape that includes non-repeating forms, repeating forms, or any combination thereof. The pattern, the conductive material, and/or the dimensions used to form the temperature sensor 702 may be configured such that the electrical properties of the temperature sensor 702 change in response to changes in temperature. For example, as the temperature of the temperature sensor 702 changes, the electrical resistance of the temperature sensor 702 can change in a predictable and/or repeatable way. Accordingly, by monitoring the changes in an electrical signal applied of the temperature sensor 702, a temperature of an object contacting the temperature sensing device in the region of the temperature sensor 702 can be detected. In some examples, the conductive material used to form the temperature sensor 702 can include platinum, nickel, copper, silver, or other suitable material, or a combination thereof.

In some embodiments, a first set of conductive traces 704 can be formed on the first side of the flexible substrate 701. The first set of conductive traces 704 can include a first conductive trace 704a that is coupled to the first node 711a and a second conductive trace 704b that is coupled to the second node 711b. The first conductive trace 704a can electrically couple the temperature sensor 702 to a first electrical interconnect 708a and the second conductive trace can electrically couple the temperature sensor 702 to a second electrical interconnect 708b. The electrical interconnects 708 can couple the first set of conductive traces 704 positioned on the first side of the substrate to a second set of conductive traces 706 that is formed on the second side of the substrate 701. In some embodiments, the electrical interconnects 708 can include vias that are formed through the substrate 701. The second set of conductive traces 706 can include a third conductive trace 706a. The first electrical interconnect 708a can couple the first conductive trace 704a to the third conductive trace 706a, and the second electrical interconnect can couple the second conductive trace 704b to the fourth conductive trace 706b. The second set of conductive traces 706 can be routed along the second side of the substrate and configured to electrically couple the temperature sensor 702 to a processing circuit 714.

In some embodiments, the temperature sensing device 700 can include connection points 710 that are used to electrically couple the temperature sensor 702 to the processing circuit 714. For example, the processing circuit 714 can be a distinct circuit from the temperature sensor stack. The connection points can include solder bumps, controlled collapse chip connections (C4 of flip chip), or any other suitable connection. In this regard, the temperature sensing device 700 can be directly coupled to an external circuit such as the processing circuit without using an interposer component.

The temperature sensing device 700 can also include a cover layer 713 that is coupled to the substrate 701 and positioned over the temperature sensor 702 and the first set of conductive traces 704. The cover layer 713 can be bonded to the flexible substrate 701 and/or one or more components that are formed on the flexible substrate 701 such as the temperature sensor 702 and the first set of conductive traces 704. In this regard, the cover layer 713 may protect electrical components positioned on the flexible substrate from water, debris, or other contaminants. Additionally or alternatively, the flexible substrate 701 and/or the cover layer 713 can reinforce the electrical components such as the temperature sensor 702 and traces to protect these components from mechanical damage. In some embodiments, the cover layer 713 can have one or more openings 712 positioned at different locations in the cover layer 713. For example, opening 712 can be positioned such that terminal ends of the second set of conductive traces 706 are exposed for coupling the temperature sensing device 700 to one or more other components such as the processing circuit 714.

The processing circuit 714 can be configured to apply an electrical signal across the conductive material of each temperature sensor 702 using the traces such as the first set of conductive traces 704 or the second set of conductive traces 706. The processing circuit 714 can also be configured to detect an effect of the temperature sensor on the electrical signal, such as a current or voltage that corresponds to a temperature of the temperature sensor 702. The processing circuit 714 can use traces such as the first set of conductive traces 704 or the second set of conductive traces 706 to detect electrical signals applied to the temperature sensor 702. In some embodiments, the processing circuit 714 determines a temperature for the temperature sensor 702 using the detected effect of the conductive material on the electrical signal. For example, the processing circuit 714 can correlate a detected electrical response such as a voltage drop, change in current, and so on to a temperature of the temperature sensor 702.

Figure 8:
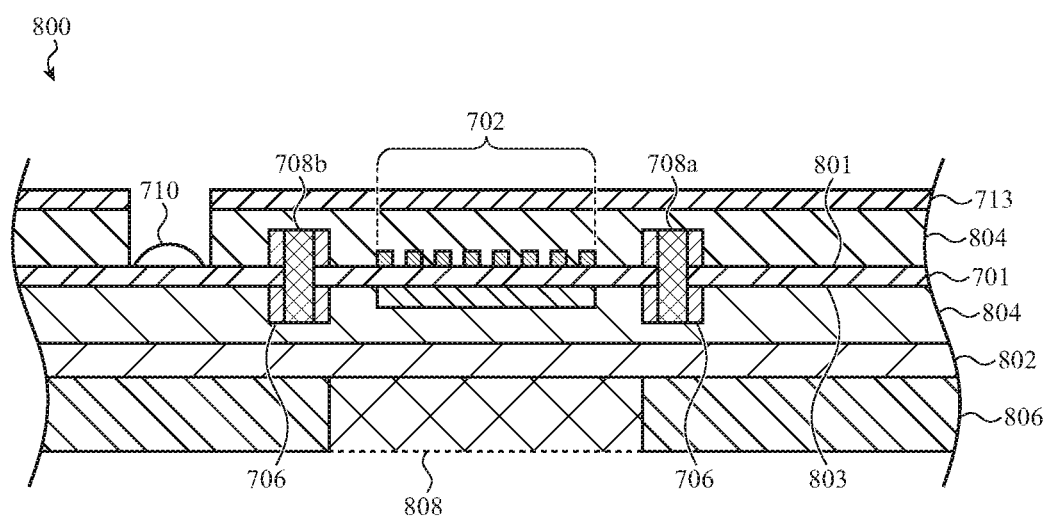
FIG. 8 shows an example cross-sectional view of the embedded temperature sensing device shown in FIG. 7.

FIG. 8 shows an example cross-sectional view of the thin film temperature sensing device 700. The cross-section of the temperature sensing device 700 is taken along section line C-C shown in FIG. 7. The temperature sensing device 700 can include the flexible substrate 701, the temperature sensor 702, the first set of conductive traces 704, the second set of conductive traces 706 and the first cover layer 713 described with reference to FIG. 3. The temperature sensor device 700 can also include a second cover layer 802, coupling material 804, a reinforcing layer 806, and a stiffener 808.

As shown in FIG. 8, the flexible substrate 701 can include a first side 801 and a second side 803. The temperature sensor 702 and the first set of conductive traces (704 shown in FIG. 7) 7 can be formed on the first side 801 of the flexible substrate 701. The second set of conductive traces 706 can be formed on the second side 803 of the flexible substrate 701. In some cases, the coupling material 804 can couple the cover layer 713 to the flexible substrate 701. The coupling material 804 can be an adhesive material and conform to the surface of the substrate 701 and features formed on the flexible substrate 701. For example, the coupling material 804 can surround the conductive material forming the temperature sensor 702 and/or conductive traces such as the first set of conductive traces 704. In this regard, the coupling material 804 may form an adhesive layer that couples the cover layer 713 to the flexible substrate 701. The coupling material 804 in combination with the cover layer 713 can form a protective layer(s) over the temperature sensor 702 and traces that can help protect these components from moisture, dust, debris, or other contaminants as well as provide mechanical protection to these components. In some embodiments, the coupling material 804 and/or the cover layer 713 can be formed from flexible materials that allow the temperature sensing device 700 to bend and/or otherwise conform to various uneven surfaces.

In some embodiments, the stiffener 808 can be coupled to the second side 803 of the flexible substrate 701. The stiffener 808 can be positioned in the region, such as a footprint, of the temperature sensor 702. In some cases, the shape and size of the stiffener 808 can be configured such that it corresponds to a shape and size of the temperature sensor 702. For example, the stiffener 808 may be sized to be the same size as or slightly bigger than the footprint of the temperature sensor 702 such that the edges of the stiffener extend to or past the outer profile of the temperature sensor 702. In other cases, the stiffener 808 can be sized to be smaller than the footprint of the temperature sensor 702 such that the edges of the stiffener do not extend past the outer profile of the temperature sensor 702. The stiffener 808 can be formed from a material that is more rigid than the flexible substrate 701, to increase the bending resistance of the flexible substrate 701 in the region of the temperature sensor 702. In this regard, the temperature sensor 702 may undergo less deformation than other portions of the temperature sensing device 700. Such configuration may protect the temperature sensor 702 from cracking or otherwise breaking as the temperature sensing device 700 deforms to accommodate different surfaces or movements of a user. In some cases, the stiffener 808 can be coupled to the second side of the flexible substrate 701. The stiffener 808 can be located on a reinforcing layer 806 that includes one or more stiffeners corresponding to temperature sensors in the array, and a flexible material that is positioned between different stiffeners. In this regard, the temperature sensing device 700 can be stiffer in the regions of the temperature sensors 702 and remain flexible in other regions.

Figure 9:
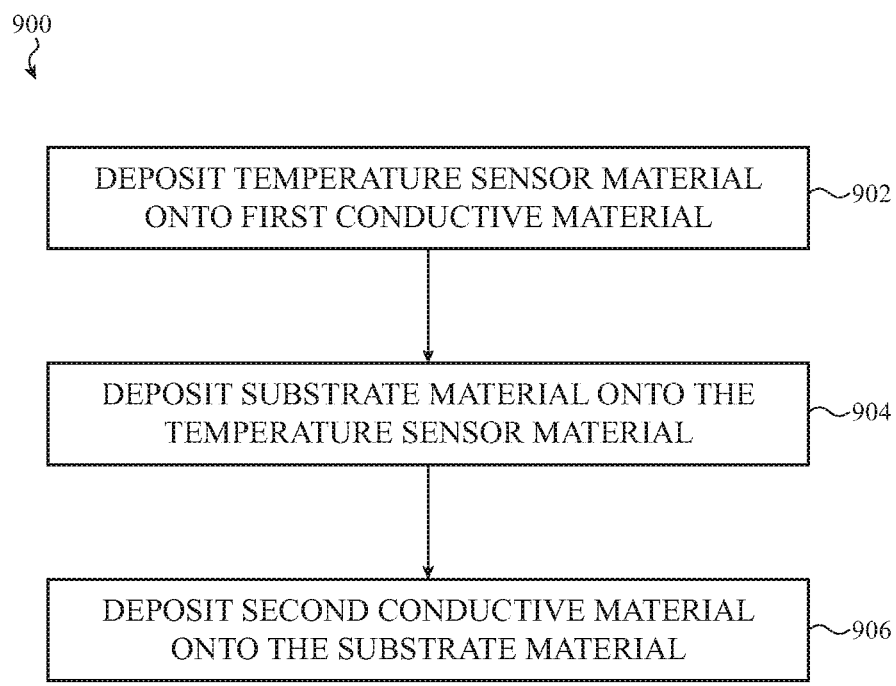
FIG. 9 shows an example process for forming a material stack used to create an embedded temperature sensing device.

FIG. 9 shows an example process 900 for forming a material stack used to create an embedded temperature sensing device. The process 900 can include coupling multiple layers of material together to form a material stack where each layer has a uniform thickness. For example, if the material stack is formed as a rectangular sheet, then each layer can have substantially the same rectangular dimensions and be coupled to form the material stack.

At 902, the process 900 can include depositing a first material that is used to form the temperature sensors onto a second conductive material that is different from the first material. For example, the first material can include a first conductive metal that will be used to form the structure of the temperature sensors and the second material can include a second conductive metal that will be used to form the one or more traces or other electrical component of the temperature sensing device. In some cases, the first material can be formed from a platinum material, nickel material, copper material, or other conductive material, and the second material can be formed from the same or a different one of a platinum material, nickel material, copper material, or other conductive material. In some cases, the first material and/or second material can be a freestanding foil material. The first material can be coupled with the second material using one or more processes such as sputtering, plating, alloy cladding, or other suitable process.

At 904, the process 900 can include coupling a substrate material onto the first material, such that the first material is positioned between the second material and the substrate material. The substrate material can be an electrically insulating material or any other suitable circuit board material. In some cases, the substrate material can be a polyimide material. The substrate material can be configured to be a flexible material such that the resulting temperature sensing device can conform to various surfaces and/or user movements.

At 906, the process 900 can include depositing a third conductive material onto the substrate material. Accordingly, the material stack can include the second and third conductive materials sandwiching the first temperature sensor material, and the substrate material. In some cases, the third conductive material can include a second conductive metal that will be used to form the one or more traces or other electrical component of the temperature sensing device. The third conductive material can be formed from the same or different material as the second conductive material.

Figure 10:
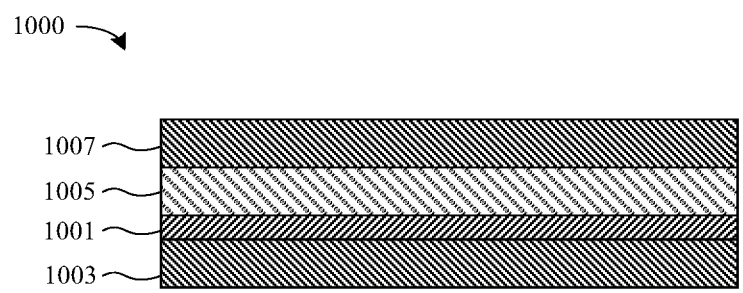
FIG. 10 shows an example cross-sectional view of a material stack that can be created using the process described herein.

FIG. 10 shows an example cross-sectional view of a material stack 1000 that can be created using the process described with reference to FIG. 9. The material stack 1000 can include a first material 1001 coupled to a second material 1003, a substrate material 1005 that is coupled to the first material 1001, and a third material 1007 that is coupled to the substrate material 1005. The first material can be used to form a temperature sensing device, the second material 1003 and the third material 1007 can be used to form one or more electrical components such as conductive traces, and the substrate material, and the substrate material 1005 can form a substrate layer of a temperature sensing device as described herein.

Figure 11:
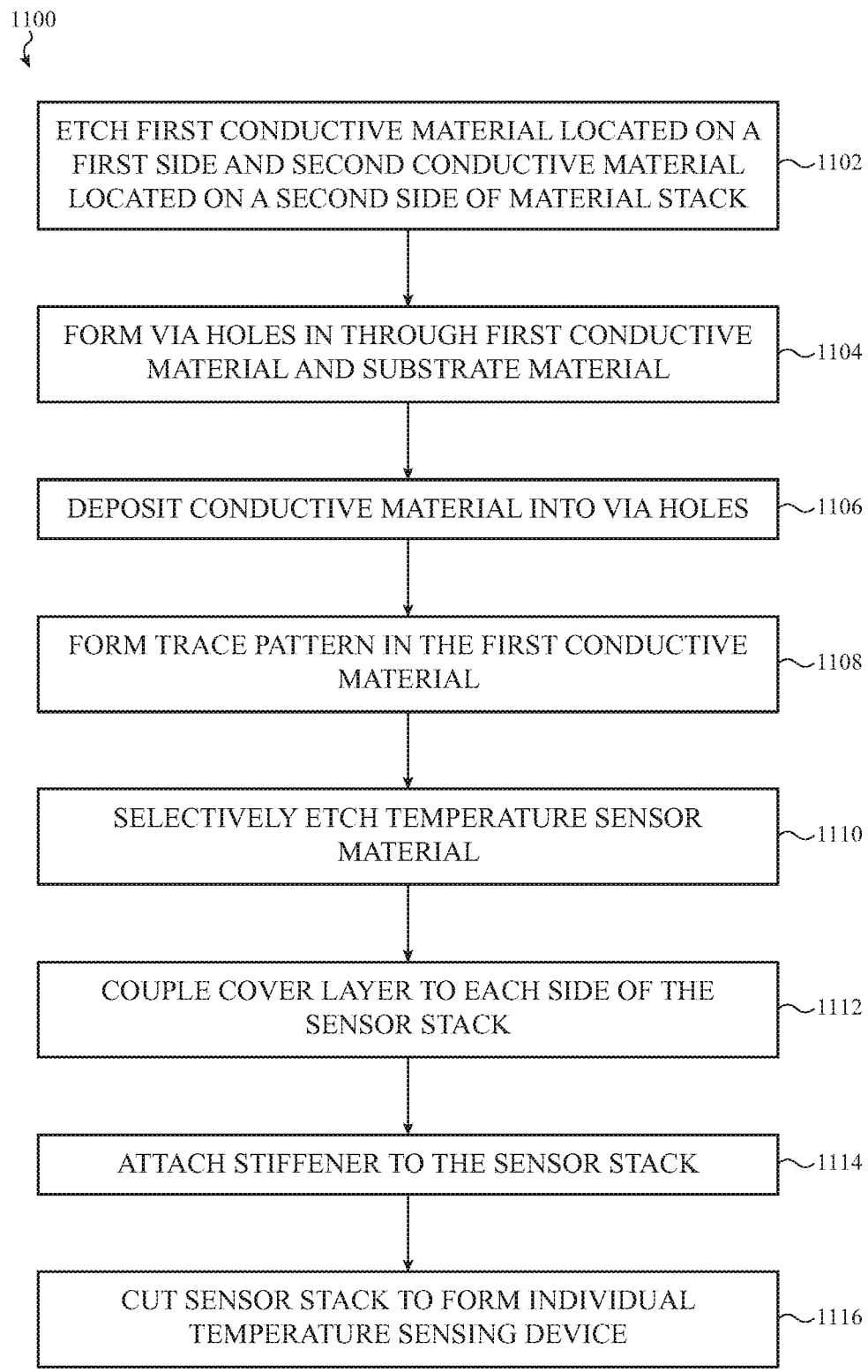
FIG. 11 shows an example process for processing a material stack to form an embedded temperature sensing device.

FIG. 11 shows an example process 1100 for processing a material stack to form an embedded temperature sensing device. The process 1100 can be performed on a material stack that includes multiple different material layers that are used to form different parts of the embedded temperature sensing device, such as the material stack discussed in relation to FIGS. 9 and 10.

At 1102, the process 1100 can include etching a first conductive material that is located on a first side of the material stack and etching a second conductive material that is located on a second side of the material stack. The stack can include a substrate layer that has the temperature sensor material and first conductive material coupled to a first side of the substrate and the second conductive material coupled to the second side of the substrate. The first and second conductive materials can be outer layers of the stack that are used to create traces or other electrical routing features on the temperature sensing device. In some cases, the etching can be used to form via holes in the first conductive material and conductive traces in the second conductive material, where the conductive traces can be used to electrically couple the temperature sensors to one or more processing circuits. In some embodiments the first and second conductive materials include a copper material, a silver material, or other suitable conductor.

At 1104, the process 1100 includes forming via holes through the substrate. The vias can be used to connect the first conductive material on the first side of the substrate with traces formed from the second conductive material on the second side of the substrate. In this regard, the traces that are used to couple a temperature sensor to the processing circuit traverse both the first side and second side of the substrate and be connected by one or more vias. At 1106, the process 1100 can include depositing a conductive material into the vias created in step 1104, to complete electrical connections between the traces formed from the first conductive material and the traces formed from the second conductive material. In some cases, step 1106 can include plating a conductive material in the vias, which can be the same or different conductive material as the first and/or second conductive materials.

At 1108, the process 1100 includes forming a trace pattern in the first conductive material. The trace pattern in the first conductive material can electrically couple temperature sensors in the first side of the device to one or more vias, such that electrical signals to and from the temperature sensors can be routed along both the first and second sides of the temperature sensing device. In some cases, forming the trace pattern can include etching both the first conductive material and the temperature sensor material to remove these materials along defined portions of the substrate. This etching can form distinct traces in the first conductive material and temperature sensing material that are electrically isolated from each other and used to carry electrical signals to and from different portions of the temperature sensing device such as different temperature sensors.

At 1110, the process 1100 can include selectively removing the first conductive material from the temperature sensing material to form the temperature sensors on the substrate. In this regard, the combination of steps 1108 and 1110 can be used to form the structure of the temperature sensors on the substrate. In step 1108, the structure of the temperature sensors is formed in both the first conductive material and the underlying temperature sensing material. Then at step 1110, the first conductive material is removed to leave the temperature sensing material in the desired structure of the temperature sensors.

At 1112, the process 1100 can include coupling a cover layer to each of the first and second sides of the sensor stack. The cover layers can be adhesively bonded to each side of the sensor stack such as by using an optically clear adhesive or any other suitable material.

At 1114, the process 1100 can include attaching one or more stiffeners to the stack. The stiffeners can each be coupled to the stack in the region of the temperature sensors to increase the rigidity of the sensor stack in the region of each temperature sensor. The stiffener can reduce stress experienced by the temperature sensors, for example, due to bending or other deformation to help ensure the temperature sensors remain functional as the temperature sensing device is used. The stiffeners can be bonded to the stack using an adhesive or other suitable process.

At 1116, the process 1100 can include cutting the sensor stack to form multiple temperature sensing devices. In some cases, each temperature sensing device can include multiple temperature sensors. For example, the sensor stack can be cut such that each temperature sensing device comprises a strip having a one-dimensional array of temperature sensors extending along a length of the strip.

Figure 12:
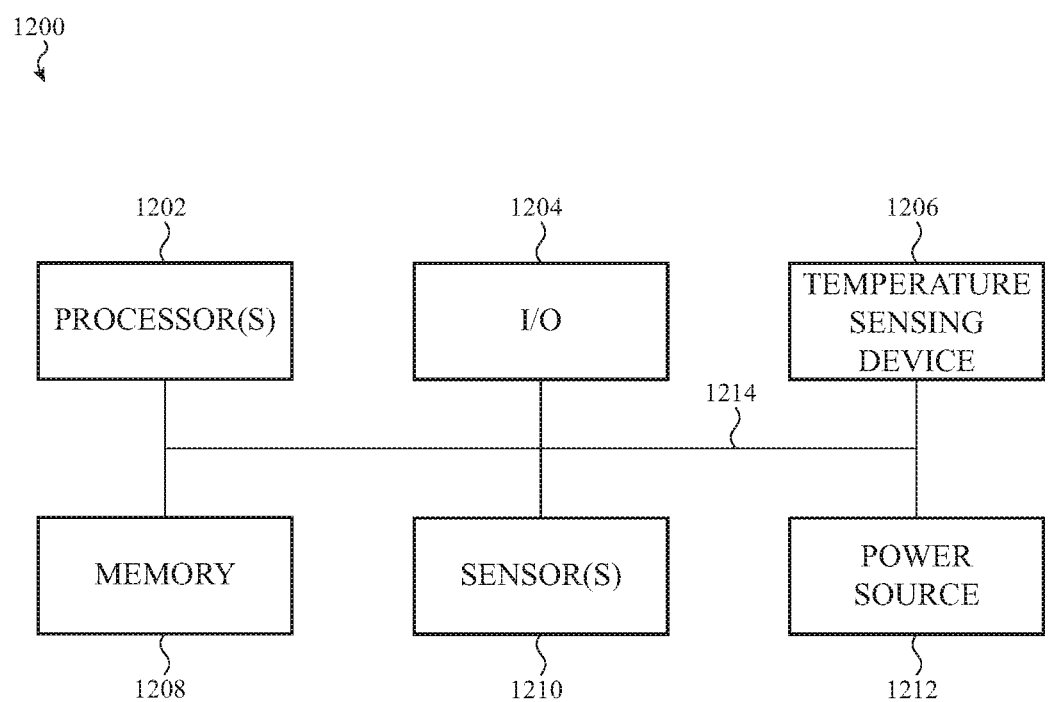
FIG. 12 is an example block diagram of a temperature sensing device.

FIG. 12 is an example block diagram of a temperature sensing device 1200, which can take the form of any of the temperature sensing systems as described with references to FIGS. 1-11. The temperature sensing system 1200 can include a processor 1202, an input/output (I/O) mechanism 1204 (e.g., an input/output device, such as a touch screen, crown or button, input/output port, or haptic interface), one or more temperature sensing devices 1206, memory 1208, other sensors 1210 (e.g., an optical sensing system, barometric pressure sensors, etc.), and a power source 1212 (e.g., a rechargeable battery). The processor 1202 can control some or all of the operations of the temperature sensing system 1200. The processing circuit 1202 can communicate, either directly or indirectly, with some or all of the components of the temperature sensing system 1200. For example, a system bus or other communication mechanism 1214 can provide communication between the processing circuit 1202, the I/O mechanism 1204, the temperature sensing device 1206, the memory 1208, the sensors 1210, and the power source 1212.

The processing circuit 1202 can be implemented as any electronic device capable of processing, receiving, or transmitting data or instructions. For example, the processing circuit 1202 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the electronic device 1200 can be controlled by multiple processors. For example, select components of the temperature sensing system 1200 (e.g., a sensor 1210) may be controlled by a first processor and other components of the temperature sensing system 1200 and other components of the temperature sensing system 1200 (e.g., the temperature sensing device 1206) may be controlled by a second processor, where the first and second processors may or may not be in communication with each other.

The I/O device 1204 can transmit and/or receive data from a user or another electronic device. An I/O device can include a display, a touch-sensing input surface, one or more buttons (e.g., a graphical user interface "home" button), one or more cameras, one or more microphones or speakers, one or more ports, such as a microphone port, and/or a keyboard. Additionally or alternatively, an I/O device 1204 or port can transmit electronic signals via a communications network, such as a wireless and/or wired network connection. Examples of wireless and wired network connections include, but are not limited to, cellular, Wi-Fi, Bluetooth, IR, and Ethernet connections.

The temperature sensing device 1206 can be any of, or include a combination of, features of the temperature sensing devices described herein, such as temperature sensing devices 102, 200, 300. In some cases, the temperature sensing system 1200 can include multiple temperature sensing devices 1206.

The memory 1208 can store electronic data that can be used by the temperature sensing system 1200. For example, the memory 1208 can store electrical data or content such as, for example, audio and video files, documents and applications, device settings and user preferences, timing signals, control signals, and data structures or databases. The memory 1208 can be configured as any type of memory. By way of example only, the memory 1208 can be implemented as random access memory, read-only memory, Flash memory, removable memory, other types of storage elements, or combinations of such devices.

The temperature sensing system 1200 may also include one or more sensors 1210 positioned almost anywhere on the electronic device 1200. The sensor(s) 1210 can be configured to sense one or more types of parameters, such as but not limited to, pressure, light, touch, heat, movement, relative motion, biometric data (e.g., biological parameters), and so on. For example, the sensor(s) 1210 may include a heat sensor, a position sensor, a light or optical sensor, an accelerometer, a pressure transducer, a gyroscope, a magnetometer, a health monitoring sensor, and so on. Additionally, the one or more sensors 1210 can utilize any suitable sensing technology, including, but not limited to, capacitive, ultrasonic, resistive, optical, ultrasound, piezoelectric, and thermal sensing technology.

The power source 1212 can be implemented with any device capable of providing energy to the temperature sensing system 1200. For example, the power source 1212 may be one or more batteries or rechargeable batteries. Additionally or alternatively, the power source 1212 can be a power connector or power cord that connects the temperature sensing system 1200 to another power source, such as a wall outlet.

As described above, one aspect of the present technology is determining, measuring, tracking and/or monitoring body temperatures of a user, and the like. The present disclosure contemplates that in some instances this gathered data may include personal information data that uniquely identifies or can be used to contact or locate a specific person. Such personal information data can include demographic data, location-based data, telephone numbers, email addresses, twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:
1. A temperature sensing device comprising:
a temperature sensor stack comprising:
a flexible substrate; and
an array of temperature sensors coupled to the flexible substrate, each temperature sensor in the array of temperature sensors comprising:

a conductive material forming a continuous pattern on the flexible substrate that extends from a first node to a second node;
a first conductive trace positioned on the flexible substrate and coupled to the first node; and
a second conductive trace positioned on the flexible substrate and coupled to the second node;
one or more stiffeners each coupled to the flexible substrate in a region of a respective temperature sensor; and
a processing circuit configured to:
apply an electrical signal across the conductive material of each temperature sensor using the first and second conductive traces;
detect an effect of the conductive material of each temperature sensor on the electrical signal using the first and second conductive traces; and
determine a temperature for one or more temperature sensors in the array of temperature sensors using the detected effect of the conductive material on the electrical signal.

2. The temperature sensing device of claim 1, wherein:
the conductive material includes a first metal;
the first and second traces include a second metal, different from the first metal; and
the temperature sensor stack further comprises a cover layer coupled to the flexible substrate with the temperature sensors in the array of temperature sensors positioned between the flexible substrate and the cover layer.

3. The temperature sensing device of claim 1, wherein the temperature sensors in the array of temperature sensors are spaced apart from each other along a first dimension of the flexible substrate that is longer than and orthogonal to a second dimension of the flexible substrate.

4. The temperature sensing device of claim 1, wherein:
the conductive material comprises a nickel material; and
the first and second conductive traces comprise the nickel material, a copper material, or a combination thereof.

5. The temperature sensing device of claim 1, wherein:
the temperature sensor stack is positioned within a housing;
the housing comprises a top layer that is configured to be positioned between the temperature sensor stack and a user; and
the temperature sensors are positioned between the flexible substrate and the top layer.

6. The temperature sensing device of claim 5, wherein:
the housing comprises a bottom layer opposite to the top layer; and
the one or more stiffeners are positioned between the temperature sensor stack and the bottom layer.

7. A temperature sensing device comprising:
a substrate comprising a first side and a second side;
a temperature sensor comprising a conductive material coupled to the first side of the substrate and defining a continuous pattern extending from a first node to a second node;
a first set of conductive traces on the substrate and comprising a first trace coupled to the first node and a second trace coupled to the second node, the first set of conductive traces operative to apply an electrical signal across the temperature sensor;
a second set of conductive traces on the substrate and comprising a third trace coupled to the first node and a fourth trace coupled to the second node, the second set of conductive traces operative to detect an effect of the conductive material on the electrical signal; and
a cover layer coupled to the first side of the substrate and positioned over the conductive material, the first set of conductive traces, and the second set of conductive traces; wherein:
the cover layer defines an opening; and
the first and second sets of conductive traces extend from the temperature sensor to the opening.

8. The temperature sensing device of claim 7, further comprising a stiffener coupled to the second side of the substrate and positioned in a region of the conductive material.

9. The temperature sensing device of claim 7, wherein:
the conductive material comprises a nickel material; and
the first and second sets of conductive traces comprise a silver material.

10. The temperature sensing device of claim 7, wherein:
the conductive material comprises a nickel material; and
the first and second sets of conductive traces comprise a copper material.

11. The temperature sensing device of claim 7, wherein the conductive material and the first and second sets of conductive traces comprise a copper material.

12. The temperature sensing device of claim 7, further comprising a processing circuit coupled with the first and second sets of conductive traces, wherein the processing circuit is configured to:
control the electrical signal applied across the temperature sensor; and
determine a temperature measured by the temperature sensor based on the detected effect of the conductive material on the electrical signal.

13. The temperature sensing device of claim 12, wherein:
the first and second sets of conductive traces are configured to couple with an interposer interface; and
the interposer interface couples the temperature sensor to the processing circuit.

* * * * *